United States Patent
Faithfull et al.

(10) Patent No.: US 6,390,977 B1
(45) Date of Patent: *May 21, 2002

(54) SYSTEM AND METHODS FOR MEASURING OXYGENATION PARAMETERS

(75) Inventors: Nicholas Simon Faithfull, La Jolla; Glenn Rhoades, San Diego, both of CA (US)

(73) Assignee: Alliance Pharmaceutical Corp., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/764,607

(22) Filed: Dec. 11, 1996

Related U.S. Application Data

(63) Continuation-in-part of application No. 08/487,086, filed on Jun. 7, 1995, now Pat. No. 5,634,461.

(51) Int. Cl.[7] .................................................. A61B 5/00
(52) U.S. Cl. ....................... 600/300; 600/505; 600/526; 600/483
(58) Field of Search ................................ 600/300, 368, 600/371, 324, 450, 451, 481–485, 508, 509, 544, 545, 524, 531, 533, 804, 525

(56) References Cited

U.S. PATENT DOCUMENTS

| | | | |
|---|---|---|---|
| 4,562,843 A | 1/1986 | Djordjevich et al. | 128/672 |
| 5,101,825 A | 4/1992 | Gravenstein et al. | 128/633 |
| 5,183,051 A | 2/1993 | Kraidin et al. | 128/687 |
| 5,217,019 A | 6/1993 | Hughes | 128/668 |
| 5,398,680 A | 3/1995 | Polson et al. | 128/633 |
| 5,499,627 A | 3/1996 | Steuer et al. | 128/633 |
| 5,713,856 A | 2/1998 | Eggers et al. | 604/65 |

FOREIGN PATENT DOCUMENTS

| | | |
|---|---|---|
| WO | WO9004353 | 5/1990 |
| WO | WO9007357 | 7/1990 |
| WO | WO9423643 | 10/1994 |
| WO | WO 96/39927 | 12/1996 |
| WO | WO 96/39928 | 12/1996 |

OTHER PUBLICATIONS

Katsuya, et al. "Continuous Monitoring of Oxygen Delivery and Consumption" Computing and Monitoring in Anesthesia & Intensive Care: 355–356 (Apr. 1991).

Fan, et al., Effects of Hematocrit Variation on Regional Hemodynamics and Oxygen Transport in the Dog, *Am. J. Physiol.*, H545–H552 (1980).

Kelman, Richard, Digital Computer Subroutine for the Conversion of Oxygen Tension into Saturation, *J. Applied Physiol.*, 21(4): 1375–1376 (1966).

Lundsgaard–Hansen, P., Hemodilution–New Clothes for an Anemic Emperor, *Vox Sang*, 36:321–336 (1979).

Lundsgaard–Hansen, et al., Is There a Generally Valid, Minimum Acceptable Hemoglobin Level?, *Infusionstherapie* 16:167–175 (1989).

Mohsenifar, et al., Relationship Between $O_2$ Delivery and $O_2$ Consumption in the Adult Respiratory Distress Syndrome, *Chest*, 84(3):267–271 (1983).

(List continued on next page.)

Primary Examiner—Robert L. Nasser
Assistant Examiner—Stephen Huang
(74) Attorney, Agent, or Firm—Knobbe, Martens, Olson & Bear LLP

(57) ABSTRACT

Systems are methods described for calculating, in real-time, various oxygenation parameters including total oxygen transport, mixed venous blood oxygen tension and mixed venous blood oxyhemoglobin saturation in a patient. The system preferably uses a computer, an arterial pressure line and a blood chemistry monitor to assist a physician in accurately determining when to give a patient a blood transfusion or otherwise alter the clinical management of that patient.

35 Claims, 9 Drawing Sheets

OTHER PUBLICATIONS

Faithfull, et al., A Program to Calculate Mixed Venous Oxygen Tension—A Guide to Transfusion? *Oxygen Transport to Tissue XVI 361* 41–49 eds. Hogan, et al. (1994).

Robertie, et al., Safe Limits of Isovolemic Hemodilution and Recommendations for Erythrocyte Transfusion, *Int'l Anesthesiology Clinics,* 28(4):197–204 (1980).

Severinghaus, J., Blood Gas Calculator, *J. Appl. Physiol.,* 21:1108–1116 (1966).

Shibutani, et al., Critical Level of Oxygen Delivery in Anesthetized Man, *Crit. Care Med.,* 11(8):640–643 (1983).

Hint, H., The Pharmacology of Dextran and the Physiological Background for the Clinical Use of Rheomacrodex and Macrodex, *Acta Anaethesiologica Belgica,* 2:119–138.

Product Brochure from Waters Instruments, Inc., Rochester, MN 55903–6117 for MRM™ 6000 Metabolic Analyzer in 7 pgs.

SYSTEM AND METHODS FOR MEASURING OXYGENATION PARAMETERS

This application is a continuation-in-part of U.S. patent application Ser. No. 08/487,086, filed Jun. 7, 1995, now U.S. Pat. No. 5,634,461.

FIELD OF THE INVENTION

This invention relates to systems and methods for non-invasively determining physiological parameters related to the oxygenation status of a patient. More specifically, the invention is directed to systems and methods for the real time determination of parameters associated with global tissue oxygenation in a subject.

BACKGROUND OF THE INVENTION

A problem that has long troubled physicians is how to accurately measure the oxygenation state of a patient's tissues without resorting to an invasive procedure. This is important during many medical procedures because the physician needs to know when to administer medicaments or transfuse more blood into a patient. When the oxygenation state of a patient's tissues is low, the physician may wish to transfuse more blood or other oxygen carriers to increase the oxygen transportation rate and maintain adequate cellular respiration.

In the surgical and postoperative settings, decisions regarding the need for blood transfusion normally are guided by hemoglobin (Hb) or hematocrit levels (Hct). Hematocrit is typically defined as the percentage by volume of packed red blood cells following centrifugation of a blood sample. If the hemoglobin level per deciliter of blood in the patient is high, the physician can infer that the patient has sufficient capacity to carry oxygen to the tissue. During an operation this value is often used as a trigger; i.e. if the value falls below a certain point, additional blood is given to the patient. While these parameters provide an indication of the arterial oxygen content of the blood, they provide no information on the total amount of oxygen transported (or "offered") to the tissues, or on the oxygen content of blood coming from the tissues.

For example, it has been shown that low postoperative hematocrit may be associated with postoperative ischemia in patients with generalized atherosclerosis. Though a number of researchers have attempted to define a critical Hct level, most authorities would agree that an empirical automatic transfusion trigger, whether based on Hb or Hct, should be avoided and that red cell transfusions should be tailored to the individual patient. The transfusion trigger, therefore, should be activated by the patient's own response to anemia rather than any predetermined value.

This is, in part, due to the fact that a number of parameters are important in determining how well the patient's tissues are actually oxygenated. In this regard, the patient's cardiac output is also an important factor in correlating hemoglobin levels with tissue oxygenation states. Cardiac output or CO is defined as the volume of blood ejected by the left ventricle of the heart into the aorta per unit of time (ml/min) and can be measured with thermodilution techniques. For example, if a patient has internal bleeding, the concentration of hemoglobin in the blood might be normal, but the total volume of blood will be low. In this situation, due to the inadequate venous return of blood to the heart, the cardiac output decreases to provide better circulation to the tissues. Accordingly, simply measuring the amount of hemoglobin in the blood without measuring other parameters such as cardiac output is not always sufficient for estimating the actual oxygenation state of the patient.

More specifically the oxygenation status of the tissues is reflected by the oxygen supply/demand relationship of those tissues i.e., the relationship of total oxygen transport ($DO_2$) to total oxygen consumption ($VO_2$). Hemoglobin is oxygenated to oxyhemoglobin in the pulmonary capillaries and then carried by the cardiac output to the tissues, where the oxygen is consumed. As oxyhemoglobin releases oxygen to the tissues, the partial pressure of oxygen ($PO_2$) decreases until sufficient oxygen has been released to meet the oxygen consumption ($VO_2$). Although there have been advances in methods of determining the oxygenation status of certain organ beds (e.g., gut tonometry; near infrared spectroscopy) these methods are difficult to apply in the clinical setting. Therefore, the use of parameters that reflect the oxygenation status of the blood coming from the tissues i.e., the partial pressure of oxygen in the mixed venous blood ($PvO_2$; also known as the mixed venous blood oxygen tension) or mixed venous blood oxyhemoglobin saturation ($SvO_2$) has become a generally accepted practice for evaluating the global oxygenation status of the tissues.

Unfortunately, relatively invasive techniques are necessary to provide more accurate tissue oxygenation levels. In this respect, direct measurement of the oxygenation state of a patient's mixed venous blood during surgery may be made using pulmonary artery catheterization. To fully describe whole body oxygen transport and delivery, one catheter (a flow directed pulmonary artery [PA] catheter) is placed in the patient's pulmonary artery and another in a peripheral artery. Blood samples are then drawn from each catheter to determine the pulmonary artery and arterial blood oxygen levels. As previously discussed, cardiac output may also be determined using the PA catheter. The physician then infers how well the patient's tissue is oxygenated directly from the measured oxygen content of the blood samples.

While these procedures have proven to be relatively accurate, they are also extremely invasive. For example, use of devices such as the Swan-Ganz® thermodilution catheter (Baxter International, Santa Ana, Calif.) can lead to an increased risk of infection, pulmonary artery bleeding, pneumothorax and other complications. Further, because of the risk and cost associated with PA catheters, their use in surgical patients is restricted to high-risk or high-blood-loss procedures (e.g., cardiac surgery, liver transplant, radical surgery for malignancies) and high-risk patients (e.g., patients who are elderly, diabetic, or have atherosclerotic disease).

Among other variables, determination of the oxygenation status of the tissues should include assessment of the amount of blood being pumped toward the tissues (CO) and the oxygen content of that (arterial) blood ($CaO_2$). The product of these variables may then be used to provide a measure of total oxygen transport ($DO_2$). Currently, assessment of $DO_2$ requires the use of the invasive monitoring equipment described above. Accordingly, determination of $DO_2$ is not possible in the majority of surgical cases. However, in the intensive care unit (ICU), invasive monitoring tends to be a part of the routine management of patients; thus, $DO_2$ determinations are obtained more readily in this population.

Partial pressure of oxygen in the mixed venous blood or mixed venous blood oxygen tension ($PvO_2$) is another important parameter that may be determined using a PA catheter. Because of the equilibrium that exists between the partial pressure of oxygen ($PO_2$) in the venous blood and tissue, a physician can infer the tissue oxygenation state of the patient. More specifically, as arterial blood passes through the tissues, a partial pressure gradient exists between the $PO_2$ of the blood in the arteriole passing through the tissue and the tissue itself. Due to this oxygen pressure gradient, oxygen is released from hemoglobin in the red blood cells and also from solution in the plasma; the released $O_2$ then diffuses into the tissue. The $PO_2$ of the blood issuing from the venous end of the capillary cylinder ($PvO_2$) will generally be a close reflection of the $PO_2$ at the distal (venous) end of the tissue through which the capillary passes.

Closely related to the mixed venous blood oxygen tension ($PvO_2$) is the mixed venous blood oxyhemoglobin saturation ($SvO_2$) which is expressed as the percentage of the available hemoglobin bound to oxygen. Typically, oxyhemoglobin disassociation curves are plotted using $SO_2$ values vs. $PO_2$ values. As the partial pressure of oxygen ($PO_2$) decreases in the blood (i.e. as it goes through a capillary) there is a corresponding decrease in the oxygen saturation of hemoglobin ($SO_2$). While arterial values of $PO_2$ and $SO_2$ are in the neighborhood of 95 mm Hg and 97% respectively, mixed venous oxygen values ($PvO_2$, $SvO_2$) are on the order of 45 mm Hg and 75% respectively. As such $SvO_2$, like $PvO_2$, is indicative of the global tissue oxygenation status. Unfortunately, like $PvO_2$, it is only measurable using relatively invasive measures.

Another rather informative parameter with respect to patient oxygenation is deliverable oxygen ($dDO_2$). $dDO_2$ is the amount of the oxygen transported to the tissues ($DO_2$) that is able to be delivered to the tissues (i.e. consumed by the tissues) before the $PvO_2$ (and by implication the global tissue oxygen tension) falls below a certain value. For instance the $dDO_2(40)$ is the amount of oxygen that can be delivered to the tissues (consumed by the tissues) before $PvO_2$ is 40 mm Hg while $dDO_2(35)$ is the amount consumed before the $PvO_2$ falls to 35 mm Hg.

Additional relevant parameters may be determined non-invasively. For instance, whole body oxygen consumption ($VO_2$) can be calculated from the difference between inspired and mixed expired oxygen and the minute volume of ventilation. Cardiac output may also be non-invasively inferred by measuring arterial blood pressure instead of relying on thermodilution catheters. For example, Kraiden et al. (U.S. Pat. No. 5,183,051, incorporated herein by reference) use a blood pressure monitor to continuously measure arterial blood pressure. These data are then converted into a pulse contour curve waveform. From this waveform, Kraiden et al. calculate the patient's cardiac output.

Regardless of how individual parameters are obtained, those skilled in the art will appreciate that various well established relationships allow additional parameters to be derived. For instance, the Fick equation (Fick, A. Wurzburg, *Physikalisch edizinische Gesellschaft* Sitzungsbericht 16 (1870)) relates the arterial oxygen concentration, venous oxygen concentration and cardiac output to the total oxygen consumption of a patient and can be written as:

$$(CaO_2-CvO_2) \times CO = VO_2$$

where $CaO_2$ is the arterial oxygen content, $CvO_2$ is the venous oxygen content, CO is the cardiac output and $VO_2$ represents whole body oxygen consumption.

While the non-invasive derivation of such parameters is helpful in the clinical setting, a more determinative "transfusion trigger" would clearly be beneficial. If $PvO_2$ or $DO_2$ is accepted as a reasonable indicator of patient safety, the question of what constitutes a "safe" level of these parameters arises. Though data exists on critical oxygen delivery levels in animal models, there is little to indicate what a critical $PvO_2$ might be in the clinical situation. The available data indicate that the level is extremely variable. For instance, in patients about to undergo cardiopulmonary bypass, critical $PvO_2$ varied between about 30 mm Hg and 45 mm Hg where the latter value is well within the range of values found in normal, fit patients. Safe $DO_2$ values exhibit similar variability.

For practical purposes a $PvO_2$ value of 35 mm Hg or more may be considered to indicate that overall tissue oxygen supply is adequate, but this is implicit on the assumption of an intact and functioning vasomotor system. Similarly, the accurate determination of $DO_2$ depends on an intact circulatory system. During surgery it is necessary to maintain a wide margin of safety and probably best to pick a transfusion trigger (whether $DO_2$, $PvO_2$, $SvO_2$ or some derivation thereof) at which the patient is obviously in good condition as far as oxygen dynamics are concerned. In practice, only certain patients will be monitored with a pulmonary artery catheter. Accordingly, the above parameters will not be available for all patients leaving the majority to be monitored with the imperfect, and often dangerous, trigger of Hb concentration.

Efforts to resolve these problems in the past have not proven entirely successful. For example, Faithfull et al. (*Oxgen Transport to Tissue XVI*, Ed. M. Hogan, Plenum Press, 1994, pp. 41–49) describe a model to derive the oxygenation status of tissue under various conditions. However, the model is merely a static simulation allowing an operator to gauge what effect changing various cardiovascular or physical parameters will have on tissue oxygenation. No provisions are made for continuous data acquisition and evaluation to provide a dynamic representation of what may actually be occurring. Accordingly, the model cannot be used to provide real-time measurements of a patient's tissue oxygenation under changing clinical conditions.

Accordingly it is a general object of the present invention to provide systems and methods to accurately assess, in real-time, $SvO_2$, $PvO_2$, $DO_2$, or some derivation thereof, of a patient.

It is a further object of the present invention to provide a method wherein an accurate indication of the oxygenation status of a patient is displayed in real-time without the necessity of invasive intervention.

It is yet another object to provide a single derived value that accurately reflects the oxygenation state of a patient.

SUMMARY OF THE INVENTION

These and other objects are accomplished by the methods and systems of the present invention which, in a broad aspect, provide for the real-time determination and display of one or more values that accurately reflect the global oxygenation and cardiovascular status of a patient. Moreover, the present invention provides for determination of the selected values through relatively non-invasive means. As such, the present invention may be used to safely monitor the physiological condition of patients and adjust therapeutic parameters based on the displayed values.

In preferred embodiments, the present invention provides for the determination and real-time display of physiologically important oxygenation parameters indicative of a patient's tissue oxygenation status such as, for example, total oxygen transport ($DO_2$), deliverable oxygen transport ($dDO_2$), mixed venous blood oxyhemoglobin saturation ($SvO_2$) and mixed venous blood oxygen tension ($PvO_2$). The invention may also be used to provide a supply/demand ratio ($dDO_2/VO_2$), another oxygenation paramneter, that allows a physician to accurately monitor and adjust the oxygen status of a patient using a single numerical value. It will be appreciated that the derived oxygenation parameters may be used alone or, more preferably, in combination to provide an indication as to global tissue oxygenation levels. As such, the invention may be used as a uncomplicated, real-time intervention trigger in clinical settings without the risks associated with conventional invasive monitoring equipment.

More specifically, by establishing the minimum acceptable $PvO_2$, $SvO_2$, $dDO_2$ or $DO_2$ for the individual patient, the attending physician is provided with a simple trigger point where intervention is indicated. For example, based on clinical experience a physician may determine that the $PvO_2$ of a patient should not be below 35 mm Hg or that the $DO_2$ should remain above 600 ml/min in order to provide adequate oxygenation. Preferably, the clinician will have access to each of the oxygenation parameters and can display one or more values as desired. In a particularly preferred embodiment, the system will provide a supply/demand ratio ($dDO_2/VO_2$) for a selected $PvO_2$ thereby allowing the physician to address the needs of the patient based on a single value. In this embodiment, a value of one or greater indicates the $PvO_2$ (and hence global tissue oxygenation) is higher than the established trigger point.

Particularly preferred embodiments provide a continuous (beat-to-beat) measurement of cardiac output (CO), using inputs from an indwelling catheter placed in a peripheral artery. In this respect an apparatus such as the Modelflow™ system (TNO-Biomedical Instrumentation, Amsterdam), can optionally be used in conjunction with the present invention to provide the CO measurement continuously in real-time. Cardiac output may be computed using an algorithm that simulates the behavior of the human aorta and arterial system via a three-element, nonlinear model of aortic input impedance. Cardiac output computed using this model has been validated against cardiac output determined by thermodilution. In addition to cardiac output, the following hemodynamic information can be derived from systems like Modelflow™ on a beat-to-beat basis: systolic, diastolic, and mean arterial pressure; pulse rate; stroke volume; and peripheral vascular resistance.

The present invention also determines the arterial oxygen content ($CaO_2$) of the patient for use in deriving the desired values. Specifically, in determining the arterial oxygen content ($CaO_2$), the present invention may use one or more numerical values corresponding to the patient's hemoglobin concentration, arterial oxygen tension ($PaO_2$), arterial carbon dioxide tension ($PaCO_2$), arterial pH and body temperature. These numerical values may be obtained from a blood chemistry monitor or entered manually. Particularly preferred embodiments employ a blood chemistry monitor to obtain the desired values contemporaneously with the measurement of the cardiac output values. Additionally, the oxygen consumption of the patient ($VO_2$) is determined, preferably by gas analysis or metabolic rate determination.

Accordingly, one embodiment of the present invention is relatively non-invasive method for determining, in real-time, one or more oxygenation parameters indicative of tissue oxygenation status of a patient, comprising the steps of:

storing oxygenation constants into a first computer memory;

measuring the cardiac output values (CO) of a patient in real-time, wherein the cardiac output values are saved to a second computer memory;

determining the arterial oxygen content ($CaO_2$) of a said patient; and calculating, in real-time, said one or more oxygenation parameters indicative of tissue oxygenation status of a patient.

In preferred embodiments the method will further include the step of storing a value corresponding to the whole body oxygen consumption ($VO_2$) of said patient into a third computer memory prior to said calculating step.

Preferably, the first computer memory discussed in the above method is a. random access memory (RAM). Similarly, the second computer memory and third computer memory of the above method are advantageously also random access memories.

In addition to the described methods, the present invention provides a relatively non-invasive apparatus for determining, in real-time, one or more oxygenation parameters indicative of tissue oxygenation status of a patient wherein the apparatus comprises:

a first computer memory for storing oxygenation constants;

an input derived from a relatively non-invasive source reflecting cardiac output (CO) values of a patient in real-time, wherein said cardiac output values are saved in a second computer memory;

first instructions for obtaining the arterial oxygen content ($CaO_2$) of said patient and storing said arterial oxygen content in a third computer memory; and second instructions for calculating, in real-time, one or more oxygenation parameters indicative of tissue oxygenation status of a patient.

Preferably, the first computer memory, second computer memory and third computer memory are random access memories. In addition, the computer memory can also advantageously be a computer hard disk. Further, the input reflecting the cardiac output can preferably be obtained from an arterial pressure line, transducers or pressure amplifiers. In another embodiment, the first instructions, which may use one or more numerical values to derive the $CaO_2$, can be stored in a blood chemistry monitor. Additionally, the first instructions may employ algorithms for calculating the position of the oxyhemoglobin disassociation curve as provided by the Kelman equations. Preferably the second instructions preferably comprise an application of the Fick equation.

As previously indicated, the present invention further provides methods and apparatus that may be used to monitor the tissue oxygenation status of a patient using a supply/demand ratio. Accordingly, one embodiment of the invention is directed to a relatively non-invasive method for monitoring, in real-time, tissue oxygenation status of a patient comprising the determination of a supply/demand ratio ($dDO_2/VO_2$). Similarly, another embodiment is directed to a relatively non-invasive apparatus for determining, in real-time, tissue oxygenation status of a patient, said apparatus comprising instructions for determining a supply/demand ratio ($dDO_2/VO_2$). The calculations, values and equipment necessary to provide the desired ratios are as described throughout the instant specification.

In all cases it must be emphasized that, while preferred embodiments of the invention include a blood chemistry monitor and/or pressure transducers (i.e. for CO), they are not essential components of the present invention and are not necessary for practicing the disclosed methods. For example, a physician could manually measure blood gas levels, body temperatures and Hb concentrations and then enter this information into the system via the keyboard. Other methods of measuring cardiac output could be used, such as ultrasound or thoracic impedance.

Those skilled in the art will further appreciate that oxygenation constants are numerical values primarily related to the physical characteristics of oxygen carriers or to the physiological characteristics of the patient. Such oxygenation constants include, but are not limited to, blood volume, oxygen solubility in plasma and the oxygen content of a desired unit of saturated oxyhemoglobin. Preferably one or more oxygenation constants is used in the present invention to derive the selected oxygenation parameters.

From the values obtained using oxygenation constants (for example $CaO_2$, $VO_2$ and CO), the present invention solves the Fick equation [$VO_2=(CaO_2-CvO_2) \times CO$] by calculating the mixed venous blood oxygen content ($CvO_2$) of the patient. Once the $CvO_2$ has been determined, $SvO_2$ can be calculated and the $PvO_2$ can be readily be derived using algorithms for calculating the position of the oxyhemoglobin disassociation curve such as the Kelman equations (Kelman, J. Appl. Physiol, 1966, 21(4): 1375–1376; incorporated herein by reference). Similarly, other parameters such as $DO_2$, $dDO_2$ and $dDO_2/VO_2$ may be derived from the obtained values.

Using the present invention, the clinician could continuously receive real-time data (i.e. the oxygenation parameters discussed above), giving him a complete picture of the patient's global oxygenation status. Should any of the selected parameters approach the established trigger points, appropriate actions such as pharmacological intervention, fluid loading, blood transfusion or adjustment of the ventilation profile could be undertaken in plenty of time to stabilize the subject. Thus, this continuous flow of data would allow the physician to more readily determine the etiology of the oxygenation decrease (such as, but not limited to, anemia, decreased cardiac output or hypoxia) and tailor the response appropriately.

Other objects, features and advantages of the present invention will be apparent to those skilled in the art from a consideration of the following detailed description of preferred exemplary embodiments thereof taken in conjunction with the Figures which will first be described briefly.

DETAILED DESCRIPTION OF SELECTED EMBODIMENTS

Figure 1:
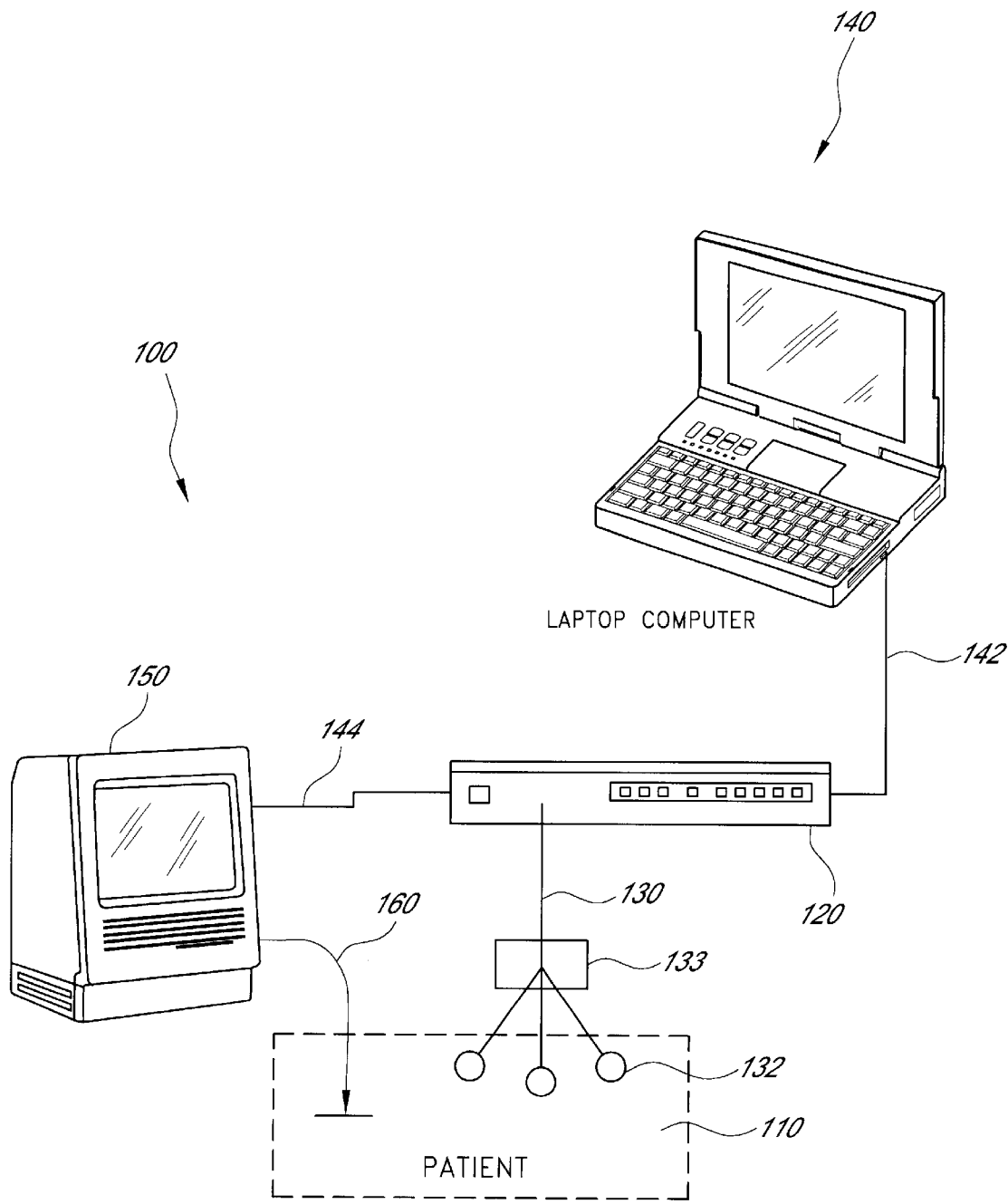
FIG. 1 is diagram of the present invention including a computer, a converter box, a blood chemistry monitor and a patient.

In a broad aspect the present invention is directed to systems, including software programs, and methods that may be used to accurately predict, in real-time, physiological parameters indicative of tissue oxygenation status or global tissue oxygenation ("oxygenation parameters"). The disclosed system and methods can be used, for example, during surgery to assist the physician in determining the appropriate time to give a blood transfusion or administer a blood substitute. By continuously calculating, for example, a patient's $PvO_2$, $SvO_2$, $DO_2$ and $dDO_2$ under a variety of clinical conditions, the system replaces the imperfect hemoglobin measurement as an indicator of global tissue oxygenation levels. In particularly preferred embodiments another oxygenation parameter, a supply/demand ratio ($dDO_2/VO_2$), is calculated and displayed in real-time.

Those skilled in the art will appreciate that the term "real-time" is used in the customary sense. That is, the derived oxygenation parameters should be updated often enough to provide a clinically useful indication of the patient's condition. Preferably, "real-time" shall mean the reporting or calculation of a condition or value (i.e. the patient's $PvO_2$ in mm Hg) not more than 1 minute after it is measurable. More preferably, the event or value will be recorded not more than 30 seconds after occurrence and, even more preferably, not more than 10 seconds. In a most preferred embodiment the condition or value is recorded not more than one heartbeat after occurrence. That is, each new heartbeat shall correspond to a recalculation of the selected oxygenation parameters.

As used herein "recorded" can mean, but is not limited to, the visual display of the derived information or its transfer to the appropriate forum for further manipulation or recognition.

Significantly, the system of the present invention has many advantages over prior art methods for measuring a patient's tissue oxygenation levels. For example, this system does not require a relatively invasive, and potentially dangerous, procedure such as pulmonary artery catheterization to determine the desired values. As used herein the term "relatively non-invasive" shall be held to mean any technique or method that does not substantially compromise the physical condition of the subject. For example, the insertion of a small cannula in a peripheral artery for the purposes of taking blood samples would be relatively non-invasive. Conversely, the insertion of a device or apparatus (such as a PA catheter) in a principal trunk artery or vein would clearly be invasive. As explained above, invasive procedures such as pulmonary artery catheterization can lead to numerous complications for the patient. Those skilled in the art will appreciate that such complications include, but are not limited to, increased incidents of infection, bleeding, pneumothorax and other complications related to the procedure.

Particularly preferred embodiments of the present invention provide a less invasive, or relatively non-invasive, method of determining mixed venous oxygenation parameters, suitable for use in conjunction with fluorocarbon-based blood substitutes, using $PvO_2$ (or $SvO_2$) both as a signal of drug activity and a component of the transfusion trigger. The present systems and methods may be used in surgeries that normally would require placement of a PA catheter, as well as in surgeries in which placement of a PA catheter could not be justified, but it nevertheless would be desirable to follow changes in cardiac output, oxygen transport and use $PvO_2$ (or $SvO_2$) as a component of a transfusion trigger.

As previously alluded to, particularly preferred embodiments of the invention employ the Fick equation to perform the desired calculations. The Fick principle states that oxygen consumption is equal to the product of the amount of blood pumped toward the tissues per minute and the difference in arterial and mixed venous oxygen content of the blood ($VO_2 = CO \times [CaO_2 - CvO_2]$); that is, $VO_2$ is equal to the oxygen supplied minus the oxygen remaining in the venous blood. If $VO_2$, cardiac output, and $CaO_2$ are known, $CvO_2$ can be calculated. Software programs compatible with the present invention use cardiac output, hemoglobin concentration, arterial blood gases, and body temperature, along with algorithms for $VO_2$ (if direct measurement is not available), $PvCO_2$, and pHv, to "back-calculate" from $CvO_2$, via $SvO_2$, to $PvO_2$, the remaining unknown value in the equation.

Those skilled in the art will appreciate that the disclosed systems comprise several components which, acting together, provide the present invention.

I. SYSTEM OVERVIEW

In preferred embodiments the present invention comprises a system that allows online, real-time monitoring of physiological parameters such as cardiac output (CO), total oxygen transport ($DO_2$), deliverable oxygen transport ($dDO_2$), mixed venous blood oxyhemoglobin saturation ($SvO_2$) and mixed venous blood oxygen tension ($PvO_2$). Further, preferred embodiments of the invention may be used to provide a supply/demand ratio ($dDO_2/VO_2$).

Turning now to FIG. 1, system 100 provides a physician with real-time data relating to the tissue oxygenation status of a patient. As shown in FIG. 1, patient 110 is linked to interface box 120 via arterial pressure line 130, transducer 132 and analog output pressure amplifier 133 that monitor the patient's arterial pulse wave. The interface box 120 has an RS232 serial port (not shown) which connects to a computer 140 by a serial cable 142. The interface box 120 may also contain an analog to digital converter to convert the analog signal of the arterial pressure output from transducers 132 into a digital signal. This digital signal is then passed to the computer 140 through the serial line 142. The analog signal from arterial pressure line 130 is normally sampled at 100 Hz with a resolution of 2.5 mV which is sent over the RS232 serial line and thereafter stored in buffers maintained in the computer's memory. The sampled signals are intermittently saved from the computer memory to the hard disk of the computer.

The data from arterial pressure line 130 can be used to calculate, as discussed below, the systolic, diastolic and mean pressure, pulse interval, heart rate, blood ejection time for the heart. In addition, a continuous aortic flow signal can be computed by the computer 140 from a simulated model of the aortic input impedance to calculate the left ventricular stroke volume, which can thereafter be multiplied by the heart beat to determine cardiac output. Systemic vascular resistance can be determined from the cardiac output and systemic arterial blood pressure. These computations are stored in a buffer in the computer's memory and then intermittently saved to the computer's hard disk. As discussed below, the cardiac output (CO) is used in the present invention to determine physiological parameters such as $DO_2$, $dDO_2$, $SvO_2$ and $PvO_2$.

A second RS232 serial port on the back of the interface box 120 receives data from the a second serial cable 144 that has been linked to optional blood chemistry monitor 150. The blood chemistry monitor 150 receives data relaying concentrations of specific components of the patient's arterial blood through an arterial monitoring line 160. The blood chemistry monitor 150 measures concentrations of blood components and physical parameters such as pH, hemoglobin levels, arterial oxygen partial pressure and arterial carbon dioxide partial pressures. One of ordinary skill in the art will realize that the information gathered by the blood chemistry monitor 150 can also be manually entered into the system. For example, a physician can take blood samples from the patient and determine, by standard analysis, the concentrations of the same blood components and physical parameters as measured by the blood chemistry monitor 150. The values can then be entered into the disclosed system through the keyboard.

The arterial monitoring line 160 repeatedly samples the patient's blood and transmits these specimens to the sensors of the blood chemistry monitor 150. One preferred blood chemistry monitor is the Model 1-01 Blood Gas and Chemistry Monitor (VIA Medical Corporation, San Diego, Calif.), an automated system that collects blood samples from an arterial line, analyzes the samples for arterial blood gases and hematocrit, and returns the sampled blood back to the patient. However, other similar types of blood chemistry monitors are anticipated to work in the same manner. In any event, when connected to the system, the blood chemistry monitor preferably provides an automated means of measuring several of the desired inputs. For example, the hematocrit value provided by a blood chemistry monitor is converted to hemoglobin within the system using a baseline mean corpuscular hemoglobin concentration (MCHC) value entered at the beginning of each case.

Tying all these hardware components together is system software. The software controls data gathering from the arterial pressure line 130 and blood chemistry monitor 150. These data are then used to derive the partial pressure of oxygen in the mixed venous blood and other oxygenation parameters to provide a real-time, accurate read out for the physician.

More specifically, in a preferred embodiment the software gathers arterial pressure data from the patient and uses these data to determine the patient's cardiac output. The actual method used to determine CO is not critical and the relevant data may be obtained using a variety of means. Accordingly, those skilled in the art will appreciate that any relatively non-invasive cardiac output measurement device may be used in conjunction with the present invention. In preferred embodiments the cardiac output determination can be made using the Modelflow software or methods such as those described in U.S. Pat. No. 5,183,051 to Kraiden which is incorporated herein by reference.

Along with the CO, arterial pH, hematocrit (or hemoglobin) levels, $PaO_2$, $PaCO_2$ and body temperature may be determined, preferably from the blood chemistry monitor input. Such values are useful in determining arterial oxygen content ($CaO_2$). This value may be used to derive $DO_2$ which is the product of $CaO_2$ and CO. Those skilled in the art will appreciate that the blood chemistry monitor can continually sample the patient's arterial blood at set time points to identify changes in blood gas/chemistry levels. If a change has taken place in any of the values measured by the blood chemistry monitor, the new value may be transmitted to the computer allowing a new arterial oxygen content to be determined.

In addition to the cardiac output, the total oxygen consumption ($VO_2$) of the patient can be calculated or determined through standard means known to those skilled in the art. For example, systems such as Physioflex from Physio Medical Systems, (Haarlem, Netherlands) and similar systems from Sensormedics (Lorba Linda, Calif.), and Puritan Bennett (Carlsbad, Calif.) are available to calculate total oxygen consumption.

In any case, after $VO_2$, cardiac output (CO), and arterial oxygen content ($CaO_2$) are determined, the software of the present invention applies these values to the Fick equation so that the mixed venous oxygen content ($CvO_2$) can be determined. This procedure is explained in more detail below.

Once the $CvO_2$ is known, mixed venous oxygen tension ($PvO_2$) and mixed venous blood oxyhemoglobin saturation ($SvO_2$) can be derived. Values for mixed venous pH and $PCO_2$ are assumed to have a constant (but alterable) relation to arterial pH and $PaCO_2$ respectively and these are used, along with other variables, in the Kelman equations to define the position of the oxyhemoglobin dissociation curve. Alternatively, algorithms for the calculation of $PvCO_2$ and PHv can be used. Knowing the Hb concentration, both $PvO_2$ and $SvO_2$ are derived to provide a value for $CvO_2$ (which includes contributions from Hb, plasma and PFC) equal to the value for $CvO_2$ determined from the Fick equation. The $PvO_2$ or $SvO_2$ value is then updated in real-time so that the physician always knows the oxygenation state of the patient. The method for performing these functions is described in more detail below.

II. HARDWARE DESCRIPTION

Figure 2:
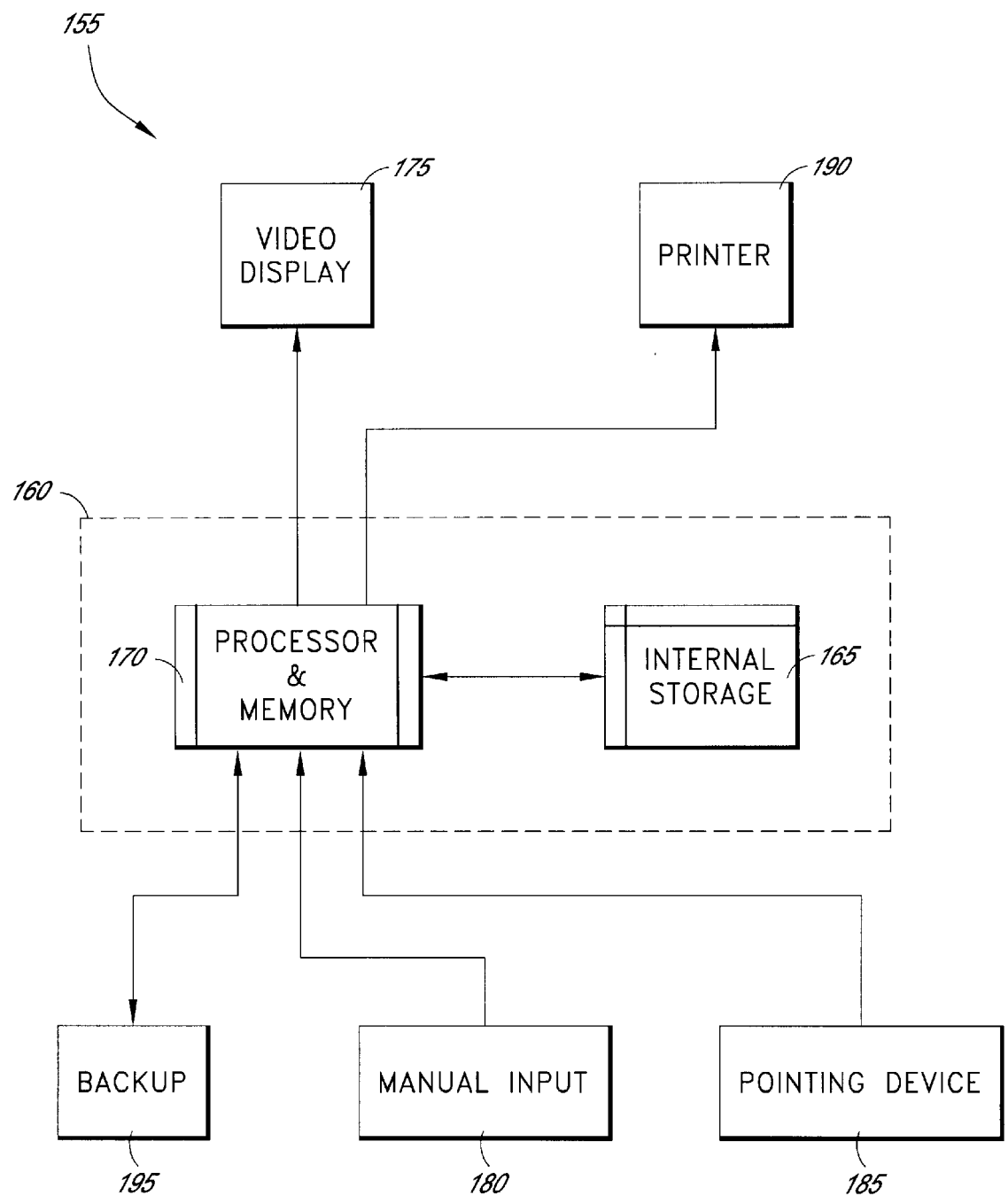
FIG. 2 is a schematic diagram of a computer system that may be used to run the present invention.

Referring now to FIG. 2, an embodiment of the computer system 155 that controls the peripheral blood monitoring system is shown. System 155 can be operated in a stand-alone configuration or as part of a network of computer systems. The system 155 is an integrated system which gathers data from the patient and presents it to the operator.

The desktop system 155 includes blood monitoring software operating in the MS-DOS, version 6.2 or later, operating system, available from Microsoft Corporation, on computer 160. Although this embodiment is described using the MS-DOS environment on a personal computer, other embodiments may use a different operational environment or a different computer or both.

In an alternate embodiment of the invention, the computer 160 can be connected via a wide area network (WAN) connection to other physicians or hospitals. A WAN connection to other medical institutions enables a real time review of the patient's progress during surgery or in the intensive care unit.

Referring again to FIG. 2, the presently preferred system 155 includes a computer 160, having a minimum of an Intel 80486 or similar microprocessor running at 33 MHz. The computer 160 includes a minimum of four megabytes (MB) of RAM memory (not shown). The system 155 includes a hard disk drive 165 connected to the processor 170. The hard drive 165 is optional in a network configuration, i.e., the workstation uses a hard disk or other storage device in a file server. If computer 160 is used in the stand-alone configuration, the hard drive 165 is preferably 100 Mbytes or more.

The computer 160 is integrated with a group of computer peripherals, and is connected to a VGA (video graphics array) display standard, or better, color video monitor 175, which is required to use all the features of the system 155.

A keyboard 180 that is compatible with IBM AT type computers is connected to the computer 160. A pointing device 185, such as a two or three button mouse can also connect to the computer 160. Reference to use of the mouse is not meant to preclude use of another type of pointing device.

The computer 160 connects to a printer 190 to provide a way to produce hard-copy output, such as printouts for file records. In this configuration, a backup device 195, such as a Jumbo 250 Mb cartridge tape back-up unit, available from Colorado Memory Systems, is preferably connected to the computer 160. A hard drive 165 or other similar device is required in the stand-alone configuration.

In an alternate embodiment of a stand-alone configuration, or as one of the workstations of a network configuration, the system 155 may include a portable computer, such as a laptop or notebook computer, e.g., a Premium Executive 386SX/20, available from AST Research, or other computers available from a plurality of vendors. The portable computer (not shown) is equipped with components similar to that described in conjunction with computer 160.

It will be understood by one skilled in the technology that a programmed computer can also be implemented completely or partially with custom circuitry. Therefore, the chosen implementation should not be considered restrictive in any matter.

III. SOFTWARE OVERVIEW

Figure 3:
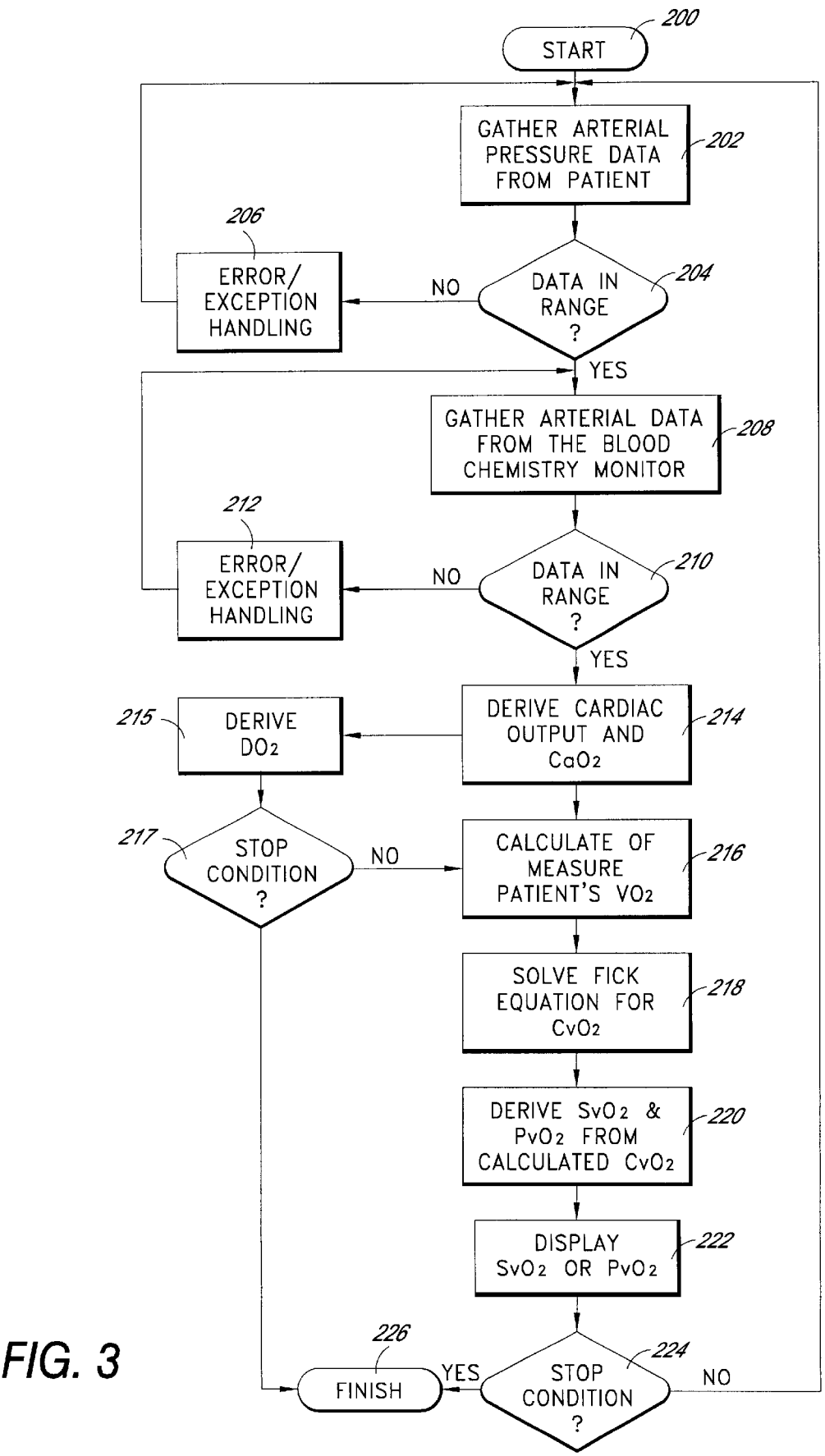
FIG. 3 is a flowchart detailing a preferred software scheme that may be used to run the present invention.

As discussed above, the systems and methods of the present invention gathers data from a patient and determines tissue oxygenation parameters of a patient in real-time. Software is used to direct this process. Those skilled in the art will appreciate that the desired parameters may be derived and displayed using various software structures written in any one of a number of languages. FIG. 3 illustrates one possible software scheme that could be used in conjunction with the disclosed methods and systems.

Referring now to FIG. 3, the process is begun when a start signal is transmitted by the user to the system at start state 200. The start signal can be a keystroke of mouse command that initiates the software to begin gathering data. After receiving the start command at state 200, arterial pressure data is gathered from a patient at state 202. Arterial pressure data is preferably gathered by hooking a patient up to an arterial pressure monitor by standard means known to those of skill in the art.

Once data have been gathered from a patient at state 202, a "data in range" decision is made at decision state 204. At this stage, the software compares the data gathered at state 202 with known appropriate ranges for arterial pressure values. Appropriate ranges for arterial pressure data are, for example, between 70/40 and 250/140.

If data gathered at process step 200 are not within the range programmed in decision state 204, or if the arterial pressure wave is abnormal an error/exception handling routine is begun at state 206. The error handling routine at state 206 loops the software back to process step 202 to re-gather the arterial pressure data. In this manner, false arterial pressure data readings will not be passed to the rest of the program. If the data gathered at process step 202 are in the appropriate range at decision state 204, the software pointer moves to process step 208 that contains instructions for gathering arterial data. Preferably the collected data will include patient temperature, arterial pH, hemoglobin levels, $PaO_2$ and $PaCO_2$. Moreover, the data is preferably generated by an attached blood chemistry monitor which may provide information on the patient's blood gas levels, acid-base status and hematology status. In such embodiments the data is gathered by receiving data streams via the serial connection from the blood chemistry monitor into the computer. Alternatively, the relevant values may be obtained from accessing data that is manually input from the keyboard.

As described previously, the blood chemistry monitor continually samples arterial blood from the patient preferably determining several properties of the patient's blood from each sample. Data corresponding to each of the properties taken from the blood chemistry monitor at process step 208 are checked so that they are in range at decision state 210. An appropriate range for the pH is 7.15 to 7.65. An appropriate range for the hemoglobin level is from 0 to 16 g/dL. An appropriate range for the $PaO_2$ is from 50 mm Hg to 650 mm Hg while an appropriate range for the $PCO_2$ is from 15 mm Hg to 75 mm Hg.

If data are not within the appropriate ranges for each specific variable at decision state 210, an error/exception handling routine at state 212 is begun. The error/exception handling routine at state 212 independently analyzes variables gathered at state 208 to determine whether it is in range. If selected variables gathered at state 208 are not within the appropriate range, the error/exception handling routine 212 loops a software pointer back to state 208 so that accurate data can be gathered. If the selected data are in range at decision box 210, the software then derives the $CaO_2$ value along with the cardiac output (CO) from the previously obtained arterial pressure data at state 214.

As discussed, cardiac output can be derived from arterial pressure measurements by any number of methods. For example, the Modelflow system from TNO Biomedical can derive a cardiac output value in real-time from an arterial pressure signal. Other methods, as discussed above, could also be used at process step 214 to determine cardiac output. Once a cardiac output value has been determined at process step 214, the patient's total oxygen transport ($DO_2$) may be derived at process step 215. As previously discussed the total oxygen transport is the product of the cardiac output and the arterial blood oxygen content. This parameter may optionally be displayed and, as indicated by decision state 217, the program terminated if the software has received a stop command. However,if the software has not received a keyboard or mouse input to stop gathering data at decision state 217, a pointer directs the program to process state 216 to derive further parameters. Specifically, process state 216 relates to the measurement or input of the patient's $VO_2$.

The patient's $VO_2$ can be calculated using the methods previously described measured by hooking the patient up to a suitable ventilator and measuring his oxygen uptake through a system such as the Physioflex discussed above or using a number of other devices such as systems manufactured by Sensormedics and Puritan Bennett. By determining the amount of oxygen inspired and expired, the ventilator may be used to calculate the total amount of oxygen absorbed by the patient. After the patient's $VO_2$ value has been determined at process step 216, these variables are applied to the Fick equation at state 218 to provide a real time $CvO_2$. The Fick equation is provided above.

Once the $CvO_2$ is known, mixed venous oxyhemoglobin saturation ($SvO_2$) and the mixed venous oxygen tension ($PvO_2$) can be derived at state 220. As previously explained, values for mixed venous pH and $PCO_2$ are assumed to have a constant (but alterable) relation to arterial pH and $PaCO_2$ respectively and these are used, along with other variables, in the Kelman equations to define the position of the oxyhemoglobin dissociation curve. Alternatively, algorithms can be derived to calculate these values. Knowing the Hb concentration a $PvO_2$ is derived that then provides a total $CvO_2$ (which includes contributions from Hb, plasma and PFC) equal to the $CvO_2$ determined from the Fick equation. If the $CvO_2$ value will not "fit" the Fick equation, another $PvO_2$ value is chosen. This process is repeated until the Fick equation balances and the true $PvO_2$ is known.

Those skilled in the art will appreciate that the same equations and algorithms may be used to derive, and optionally display, the mixed venous blood oxyhemoglobin saturation $SvO_2$. That is, $SvO_2$ is closely related to $PvO_2$ and may easily be derived from the oxygen-hemoglobin dissociation curve using conventional techniques. It will farther be appreciated that, as with $PvO_2$, $SvO_2$ may be used to monitor the patient's oxygenation state and as an intervention trigger if so desired by the clinician. As discussed above, mixed venous blood oxyhemoglobin saturation may be used alone in this capacity or, more preferably, in concert with the other derived parameters.

After deriving values for $PvO_2$, $SvO_2$ or both, the value or values may be displayed on the computer screen at step 222. If the software has not received a keyboard or mouse input to stop gathering data at decision state 224, a pointer loops the program back to process state 202 to begin gathering arterial pressure data again. In this manner, a real-time data loop continues so that the patient's mixed venous blood oxygen tension ($PvO_2$) or saturation ($SvO_2$) is constantly updated and displayed on the computer at state 222. If the software has received a stop command from a keyboard or mouse input at decision state 224, then a finish routine 226 is begun.

IV. SOFTWARE IMPLEMENTATION

Many different ways of implementing the software of the present invention will be known to those with ordinary skill in the art. For example, programming languages such as C++, Basic, Cobol, Fortran or Modula-2 can be used to integrate the features of the present invention into one software package. An alternative method of illustrating the software of the present invention is to use a spreadsheet program to gather and determine the $PvO_2$ of a patient in real-time. This method is described in detail below.

The following system utilizes a large Microsoft EXCEL® spreadsheet to gather information from the patient and display the desired parameters including $PvO_2$, $SvO_2$ and $DO_2$. Before receiving real-time inputs of cardiovascular and oxygenation variables, a number of oxygenation constants may be entered into the system. These constants preferably include the patient's estimated blood volume, oxygen solubility in plasma and the oxygen content of 1 g of saturated oxyhemoglobin. The oxygenation constants are then stored in the computer's memory for use in later calculations.

TABLE 1 shows commands from part of a Microsoft EXCEL® spreadsheet that gathers a patient's data and derives the value of the desired oxygenation parameters. The program is initialized by assigning names to various oxygenation constants that are to be used throughout the software. In the embodiment shown oxygenation constants corresponding to blood volume (BV), oxygen solubility in a perfluorocarbon emulsion ($O_2SOL$), specific gravity of any perfluorocarbon emulsion (SGPFOB), intravascular half-life of a perfluorocarbon emulsion (BL), weight/volume of a, perfluorocarbon emulsion (CONC), barometric pressure at sea level (BARO), milliliters oxygen per gram of saturated hemoglobin (HbO) and milliliters of oxygen per 100 ml plasma per 100 mm of mercury (PIO) are all entered. The constants relating to perfluorocarbons would be entered in the event that fluorocarbon blood substitutes were going to be administered to the patient.

An example of starting values for Kelman constants, a subset of the oxygenation constants, is also shown in TABLE 1. These starting values are used in later calculations to derive the patient's mixed venous oxygenation state or other desired parameters such as mixed venous blood oxyhemoglobin saturation. As with the other oxygenation constants the Kelman constants are also assigned names as shown in TABLE 1.

TABLE 1

| ASSUMPTIONS: | VALUES AT START |
|---|---|
| Blood Volume (ml/kg) -BV | 70 |
| $O_2$ solubility in PFB (ml/dl @ 37 deg C.) -O2SOL | 52.7 |
| Specific Gravity of PFOB -SGPFOB | 1.92 |
| Intravascular half-life of Oxygent HT (hours) -HL | = ½ Life of Oxygent |
| Wgt/Vol of PFOB emulsion/100 -CONC | 0.6 |
| Barometric Pressure @ sea level -BARO | 760 |
| Ml O2 per gram saturated Hb -HbO | 1.34 |
| Ml O2 per 100 ml plasma per 100 mm Hg -HIO | 0.3 |

| KELMAN CONSTANTS: | VALUES AT START |
|---|---|
| Ka1 | = −8.5322289*1000 |
| Ka2 | = 2.121401*1000 |
| Ka3 | = −6.7073989*10 |
| Ka4 | = 9.3596087*100000 |
| Ka5 | = −3.1346258*10000 |
| Ka6 | = 2.3961674*1000 |
| Ka7 | −67.104406 |

Figure 4:
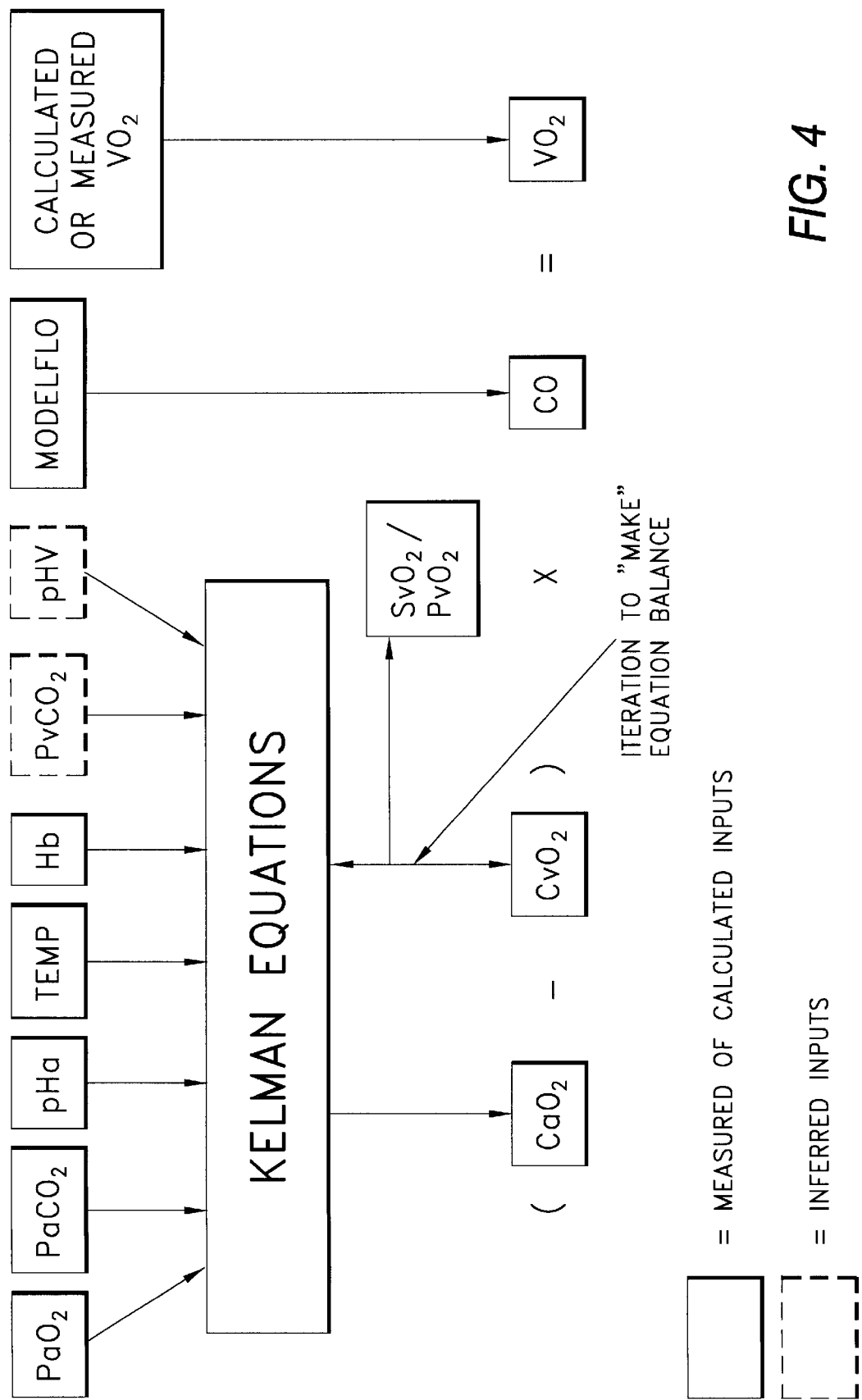
FIG. 4 is a schematic diagram of data input and calculations as performed in selected embodiments of the present invention.

After the oxygenation constants, including the Kelman constants have been assigned names, real time inputs from the arterial pressure lines and blood chemistry monitor may be initialized and begin providing data. As shown in TABLE 2, the system depicted in this embodiment derives or receives data relating to the arterial. oxyhemoglobin saturation percentage ($SaO_2$). In particular, saturation percentages are derived from arterial data for oxygen tension ($PaO_2$), pH (pHa), carbon dioxide tension. ($PaCO_2$) and body temperature (TEMP). If desired by the clinician, the present invention provides for the real-time display of $SvO_2$ values (as derived from calculated $PvO_2$, pHv, $PvCO_2$ and temperature) to be used for the monitoring of the patient's tissue oxygenation status. As previously discussed, values for $PvCO_2$ and pHv are related, by a fixed amount, to those of $PaCO_2$ and pHa respectively as determined by algorithms. Cardiac output (CO) is also input as is $VO_2$. FIG. 4 provides a schematic representation of this procedure and resulting data.

When Hb concentration, arterial blood gas and acid/base parameters are entered (automatically or manually) into the program, the $O_2$ delivery and consumption variables for both red cell containing Hb and for the plasma phase may be determined. Those variables relating to PFC (in the case of blood substitutes) or Hb based oxygen carrier can also be determined.

Referring again to FIG. 4, numerical values useful for the calculation of $CaO_2$ relate to Hb concentration, arterial oxygen tension ($PaO_2$), arterial carbon dioxide tension ($PaCO_2$), arterial pH (pHa) and body temperature. The position of the oxygen-hemoglobin dissociation curve is calculated using the Kelman equations, which are input as oxygenation constants in the program. These calculations produce a curve that, over the physiological range of $O_2$ tensions, is indistinguishable from the parent curve proposed by Severinghaus (*J. Appl. Physiol.* 1966, 21: 1108–1116) incorporated herein by reference. As shown schematically in FIG. 4, iteration may be used to calculate a $PvO_2$ (via $SvO_2$) that results in the required mixed venous oxygen contents in Hb, plasma and fluorocarbon to satisfy the Fick equation.

TABLE 2

| INPUTS: | AT START: |
|---|---|
| Hemoglobin (Gm/dl) -Hb | 6 |
| Arterial Oxyhemoglobin saturation (%) -SaO2 | |
| Calculated Arterial Oxyhemoglobin saturation (%) - SaO2CALC | = 100*(SPaO2*(SPaO2*(SPaO2*(SPaO2 + Ka3) + Ka2) + Ka1))/ (SPaO2*(SPaO2*(SPaO2*(SPa02 + Ka7) + Ka6) + Ka5) + K |
| Active Input Value for SaO2 -SaO2USED | = IF (SaO2 < > 0, SaO2, SaO2CALC) |
| Mixed venous blood oxyhemoglobin saturation (%) -SvO2 | |
| Calculated Mixed venous blood oxyhemoglobin saturation SVO2CALC | = 100*(SPvO2*(SPvO2*(SPvO2*(SPvO2 + Ka3) + Ka2) + Ka1))/ SPvO2*(SPvO2*(SPvO2*(SPv)2 + Ka7) + Ka6) + Ka5) + k |
| Active Input Value for SvO2 -SvO2USED | = IF(SvO2 < > 0, SvO2, SvO2CALC) |
| Arterial Oxygen Partial Pressure (mm Hg) -PaO2 | 100 |
| Calculated 'standardized' PaO2 -SPaO2 | = PaO2*10^((0.024*(37-TEMPUSED)) + (0.4*(pHaUSED − 7.4)) + (0.06*(LOG10(40) − LOG10(PaCO2USED)))) |
| Active Input Value for PaSO2 -PaSO2USED | = IF(PaO2 < > 0, PaO2, SPaO2) |
| Arterial pH -pHa | |
| Normal Arterial pH -pHaNORM | 7.4 |
| Active Input Arterial pH -pHaUSED | = IF(pHa < > ), pHa, pHaNORM) |
| Arterial PCO2 -PaCO2 | |
| Normal PaCO2 -PaCO2NORM | 40 |
| Active Input Arterial PCO2 -PaCO2USED | = IF(PaCO2 < > 0, PaCO2, PaCO2NORM) |
| Body Temp C. -TEMP | |
| Normal Body Temp C. -TEMPNORM | 37 |
| Active Input Body Temp C. -TEMPUSED | = IF(TEMP < > 0, TEMP, TEMPNORM) |
| Mixed Venous Oxygen Partial Pressure (mm Hg) -PvO2 | 40.6819722973629 |

TABLE 2-continued

| INPUTS: | AT START: |
|---|---|
| Calculated 'standardized' PvO2 -SPvO2 | = PvO2*10^((0.024*(37-TEMPUSED) + (0.4*(pHvUSED-7.4)) + (0.06*(LOG10(40) − LOG10(PvCO2USED)))) |
| Mixed Venous pH -pHv | |
| Normal Venous pH | 7.4 |
| Active Input Mixed Venous pH -pHvUSED | = IF(pHv < > 0, pHv, pHvNORM) |
| Mixed Venous PCO2 -PvCO2 | |
| Normal Mixed Venous PCO2 -PvCO2NORM | 40 |
| Active Input Mixed Venous PCO2 -PvCO2USED | = IF(PvCO2 < > 0, PvCO2, PvCO2NORM) |
| Cardiac Output (l/mm) -CD | = ((14 − Hemoglobin (gm/dl) * CD Response to 1 gram of Hb Depletion) + 5 |
| CD Response to 1 gr Hb depletion -COCHG | 0.7 |
| Intravascular Oxygent HT Dose (ml/kg) -PFB | |
| Time Adj. Intravascular Oxygent HT Conc (ml/kg) - TAPBF | |
| Patient's Weight (kg) -kg | 70 |
| Total O2 Consumption (ml/min/kg) -VO2KG | 3 |
| Calculated Blood Volume (ml) -CBV | = BV*kg |
| Calc input Total O2 Consumption (ml/min/kg) -VO2 | = kg*VO2KG |

TABLE 3

| DESCRIPTION: | CALCULATIONS: |
|---|---|
| Arterial O2 Content in Hemoglobin (ml/dl) - CaO2Hb | = ((Hb*HbO*SaO2USED)/100) |
| Arterial O2 Content in Plasma (ml/dl) -CaO2PI | = ((PaO2*PIO)/100) |
| Arterial O2 Content in PFB (ml/dl) -CaO2PFB | = ((PFB*kg*CONC)/SGPFOB)/(kg*BV*0.01)*((O2SOL*PaO2)/(100*BARO)) |
| Arterial Oxygen Content (ml/dl) -CaO2 | = (CaO2Hb + CaO2PI + CaO2PFB) |
| Mixed Venous O2 Content in Hemoglobin (ml/dl) -CvO2Hb | = ((Hb*HBO*SvO2USED)/100) |
| Mixed Venous O2 Content in Plasma (ml/dl) -CvO2PI | ≦ ((PvO2*PIO)/100) |
| Mixed Venous O2 Content in PFB (ml/dl) -CvO2PFB | = ((PFB*kg*CONC)/SGPFDB)/(kg*BV*0.01)*((O2SOL*PvO2)/(100*BARO)) |
| Mixed Venous Oxygen Content (ml/gl) -CvO2SUM | = (Cv)2Hb + CvO2PI + CvO2PFB) |
| Mixed Venous Oxygen Content (ml/dl) -CvO2 | = IF(CVO2SUM > 0, (CVO2SUM), CvO2CALC2) |
| Mixed Venous O2 Content (ml/dl) - CvO2CALC2 | = CaO2-(VO2/(CO*10)) |
| Percent of VO2 provided from plasma | = (O$_2$ Used From Plasma/Active Input Total O$_2$ Consumption) * 100 |
| Percent VO2 provided by PFB | = 100 * (O$_2$ Used From Perflubron/Active Input Total O$_2$ Consumption) |
| Percent of VO2 provided by plasma and PFB | = 100 * ((O$_2$ Used From Plasma + O$_2$ Used From Perflubron/Active Input Total O$_2$ Consumption) * 100 |

TABLE 4

| DESCRIPTION | OUTPUTS: |
|---|---|
| Total Oxygen Transport (ml/min) -TDO2 | = CaO2*CO*10 |
| O2 Transport in Hemoglobin ml/min) -DO2Hb | = (CaO2Hb)*CO*10 |
| O2 Transport in plasma (ml/min) -DO2PI | = CaO2PI*CO*10 |
| O2 Transport in Perflubron (ml/min) -DO2PFB | = CaO2PFB*CO*10 |
| Calc Total O2 Consumption (ml/min) -VO2CALC | = (CaO2-CvO2)*CO*10 |
| Active Input Total O2 Consumption (ml/min) -VO2USED | = IF(VO2 < > ), VO2, VO2CALC) |
| Oxygen Used from Hemoglobin (ml/min) -VO2Hb | = (CaO2Hb-CvO2Hb)*CO*10 |
| Oxygen Used from Plasma (ml/min) -VO2PI | = (CaO2PI-CvO2PI)*(CO*10) |
| Oxygen Used from Perflubron (ml/min) -VO2PFB | = (CaO2PFB-CvO2PFB)*(CO*10) |
| Total Oxygen Extraction Coefficient -OEC | = (CaO2-CvO2)/CaO2 |
| Hemoglobin Oxygen Extraction Coefficient - HOEC | = (SaO2USED-SvO2USED)/SaO2USED |

Based on the numerical values provided the program calculates and can present oxygenation parameters such as $PvO_2$ and $SvO_2$ in real time as shown in TABLE 2. As previously alluded to, this value can help the physician determine when to give the patient a blood transfusion or in other ways alter the patient's clinical management. Significantly, the displayed values may be used to monitor the physiological effects of blood substitutes including those based on hemoglobin or perfiurochemicals following their administration.

TABLE 3 and TABLE 4 show additional information that may be provided by the instant invention further demonstrating its utility and adaptability. More specifically, TABLE 3 provides various oxygenation values that may be calculated using the methods disclosed herein while TABLE 4 provides other indices of oxygen consumption and oxygen delivery that are useful in optimizing patient treatment.

A closer examination of TABLE 3 shows that the system of the present invention may be used to provide the individual oxygen content of different constituents in a mixed oxygen carrying system. In particular, TABLE 3 provides calculations that give the arterial or venous oxygen content of circulating hemoglobin, plasma and fluorochemical respectively. Such values would be of particular use when intravenously introducing fluorochemical emulsion blood substitutes in conjunction with surgical procedures.

TABLE 4 illustrates that the present invention may also be used to provide real-time information regarding oxygen consumption and delivery. As mentioned previously, Hb or Hct measurements are not a suitable reflection of tissue oxygenation. This is mainly because they only give an indication of the potential arterial $O_2$ content ($CaO_2$), without providing information about the total oxygen transport ($DO_2$) to the tissues where it is to be used. However as seen in TABLE 4 the instant invention solves this problem by providing on line oxygen transport information which is derived based on $CaO_2$ and cardiac output (CO).

Currently cardiac output is measured using thermodilution, and $CaO_2$ is calculated typically by measuring the arterial oxyhemoglobin saturation ($SaO_2$) and hemoglobin levels, and inserting these values into the following equation: $CaO_2=([Hb]\times 1.34\times SaO_2)+(PaO_2\times 0.003)$, where [Hb] =hemoglobin concentration (in g/dL); 1.34=the amount of oxygen carried per gram of fully saturated hemoglobin; $PaO_2$= the arterial oxygen tension; and 0.003 is the amount of oxygen carried by the plasma (per deciliter per mm Hg of oxygen tension).

The present invention combines the continuous cardiac output algorithm with the Kelman equations to provide the position of the oxygen hemoglobin dissociation curve. Using on-line and off-line inputs of body temperature, hemoglobin, and arterial blood gases, the present invention is able to trend $DO_2$ on a continuous basis. The factors used to determine $DO_2$ are displayed along with their product; thus, the etiology of a decrease in $DO_2$ (inadequate cardiac output, anemia, or hypoxia) would be readily apparent to the physician, decisions regarding the appropriate interventions could be made expeditiously, and the results of treatment would be evident and easily followed.

More particularly, preferred embodiments of the invention may be used to provide and display real-time $DO_2$, arterial blood gases, hemoglobin concentration and CO (and all other hemodynamic data already discussed such as BP, heart rate, systemic vascular resistance, rate pressure product and cardiac work). As shown in TABLE 3, such embodiments can also provide separate readouts of contributions of Hb, plasma and PFC (if in circulation) to $DO_2$. That is, the oxygen contributions of each component may be accurately monitored and adjusted throughout any therapeutic regimen. Such data would be particularly useful in both the OR and ICU for providing a safety cushion with respect to the oxygenation of the patient.

The importance of maximizing $DO_2$ for certain patients in the ICU has been underscored by recent studies. The present invention may also be used for determining when such intervention is indicated and to provide the data necessary for achieving the desired results. Once $DO_2$ is known it is possible to calculate the maximum $O_2$ consumption ($VO_2$) that could be supported for a certain chosen (and alterable) $PvO_2$. As previously discussed, this value may be termed deliverable oxygen ($dDO_2$). For instance, a $PvO_2$ of 36 mm Hg might be chosen for a healthy 25 year old patient, where as a $PvO_2$ of 42 mm Hg or higher might be needed for an older patient with widespread arteriosclerosis or evidence of coronary atheroma or myocardial ischemia. Oxygen consumption under anesthesia is variable, but almost always lies in the range of 1.5 to 2.5 ml/kg/min. If the supportable $VO_2$, at the chosen $PvO_2$, was well above this range all would be well and no intervention would be necessary. The closer the supportable $VO_2$ to the normal $VO_2$ range the earlier intervention could be considered.

This relationship could be used to provide a single value, based on deliverable oxygen ($dDO_2$) vs. oxygen consumption ($VO_2$), that would simplify patient care. As previously explained, $dDO_2$ is the amount of oxygen transported to the tissue that is able to be delivered before the partial venous oxygen pressure ($PvO_2$) and, by implication, tissue oxygenation tension falls below a defined level. Thus, if it is desired that the $PvO_2$ value not fall below 40 (this number is variable for different patients depending on their general medical condition) then $DO_2$ (and by implication $dDO_2$) must be maintained at sufficient levels. The supply/demand ratio ($dDO_2/VO_2$) for a selected $PvO_2$ can be used to provide a single value showing the that the amount of oxygen being administered is sufficient to maintain the desired oxygenation state. For example, if it is known that the $dDO_2$ required to maintain a $PvO_2$ of 40 is say 300 ml/min and the measured ($VO_2$) is 200 ml/min then the patient is being supplied with enough oxygen for his needs. That is, the supply/demand ratio is 300 ml/min÷200 ml/min or 1.5. A supply/demand ratio of 1 would imply that the $PvO_2$ (or other selected parameter i.e. $SvO_2$) was at the selected trigger value (here 40 mm Hg). Conversely, if the $dDO_2(40)$ (deliverable oxygen) is 200 ml/min and the $VO_2$ (oxygen consumption) is 300 ml/min then the ratio is 0.66 and the patient is not receiving sufficient oxygen (i.e. the $PvO_2$ will be less than 40). Continuous monitoring and display of this ratio will allow the clinician to observe the value approaching unity and intervene appropriately.

EXAMPLE I

To evaluate the accuracy of the present invention for calculation of $PvO_2$, a pilot study was conducted in Europe in which $PvO_2$ levels derived using the disclosed systems were compared to directly measured $PvO_2$ values. In this study, 17 subjects undergoing surgeries for which placement of an arterial line and PA catheter was indicated were enrolled, and a series of measurements was taken to provide inputs for the $PvO_2$ calculations using the instant invention. The measurements were taken as frequently as possible during surgery, at inspired oxygen ($FiO_2$) levels ranging from 0.4 to 0.8 (to obtain a wide range of $PvO_2$ values), and at 30-minute intervals during a 6-hour period in the recovery room. As discussed, variables used for determination of $PvO_2$ in the present invention can include cardiac output, arterial hemoglobin, blood gases, $VO_2$, and body temperature. In this study, continuous cardiac output was determined on-line within the system as described previously (i.e. using the Modelflo apparatus); hemoglobin, arterial blood gases, and body temperature were measured using standard techniques and entered manually into the system; intraoperative $VO_2$ was measured using the PhysioFlex closed-circuit anesthetic machine (Physio B. V., Haarlem, The Netherlands), and entered manually into the system; postoperative $VO_2$ was determined through the disclosed system using an algorithm and $PvCO_2$ and pHv were calculated within the system using generally accepted approximations of arteriovenous differences in $PCO_2$ and pH ($PvCO_2$= $PaCO_2$ +4; pHv=pHa−0.03). Mixed venous blood was withdrawn from the pulmonary artery simultaneously with the arterial samples, and $PvO_2$, $PvCO_2$, and pHv were analyzed using standard blood gas analysis techniques. $PvO_2$ values derived by the system and those measured and analyzed using standard methods were compared.

Figure 5:
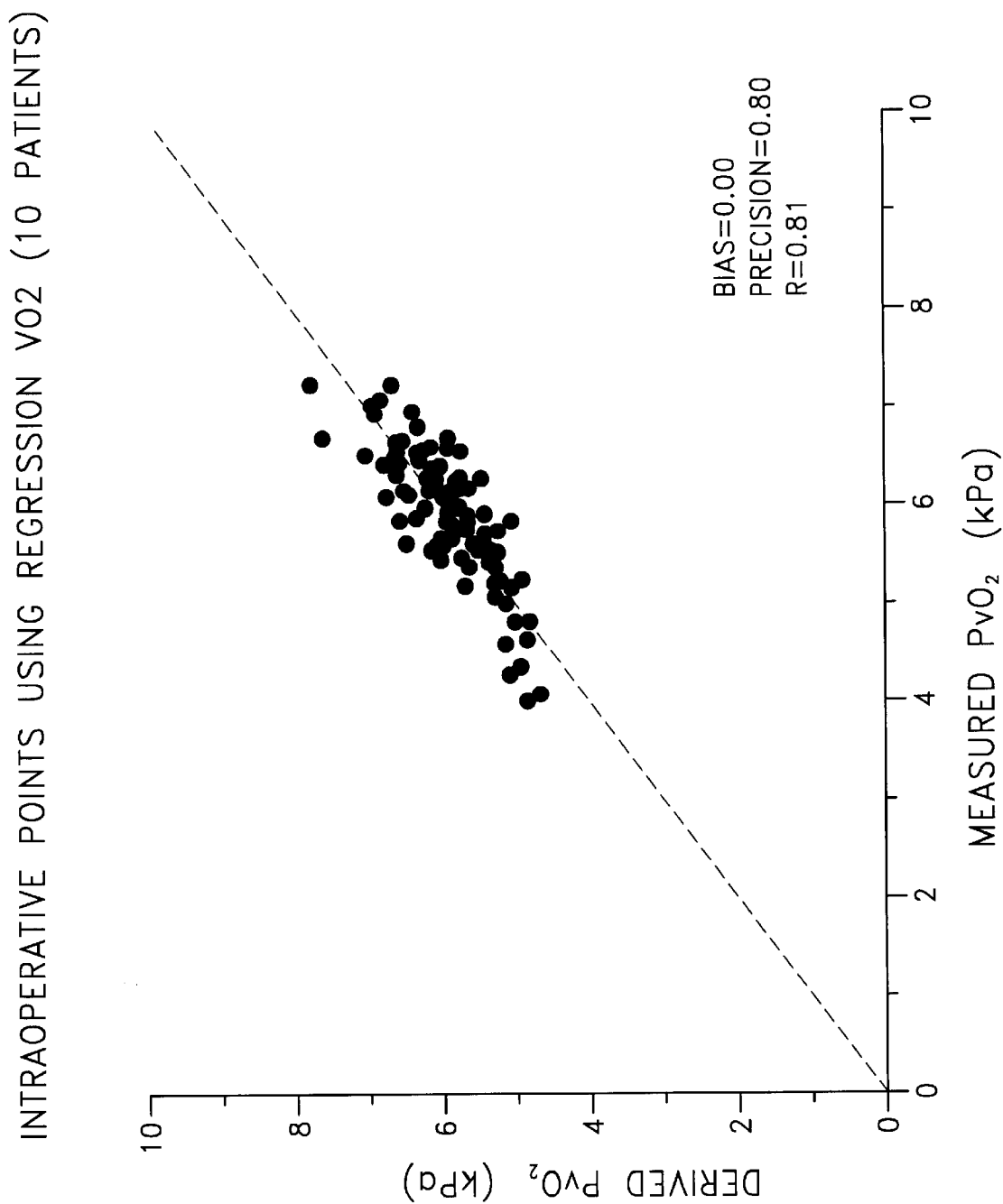
FIG. 5 is a graphical representation of intraoperative $PvO_2$ values derived from a PA catheter vs. intraoperative $PvO_2$ values derived using the present invention.
Figure 6:
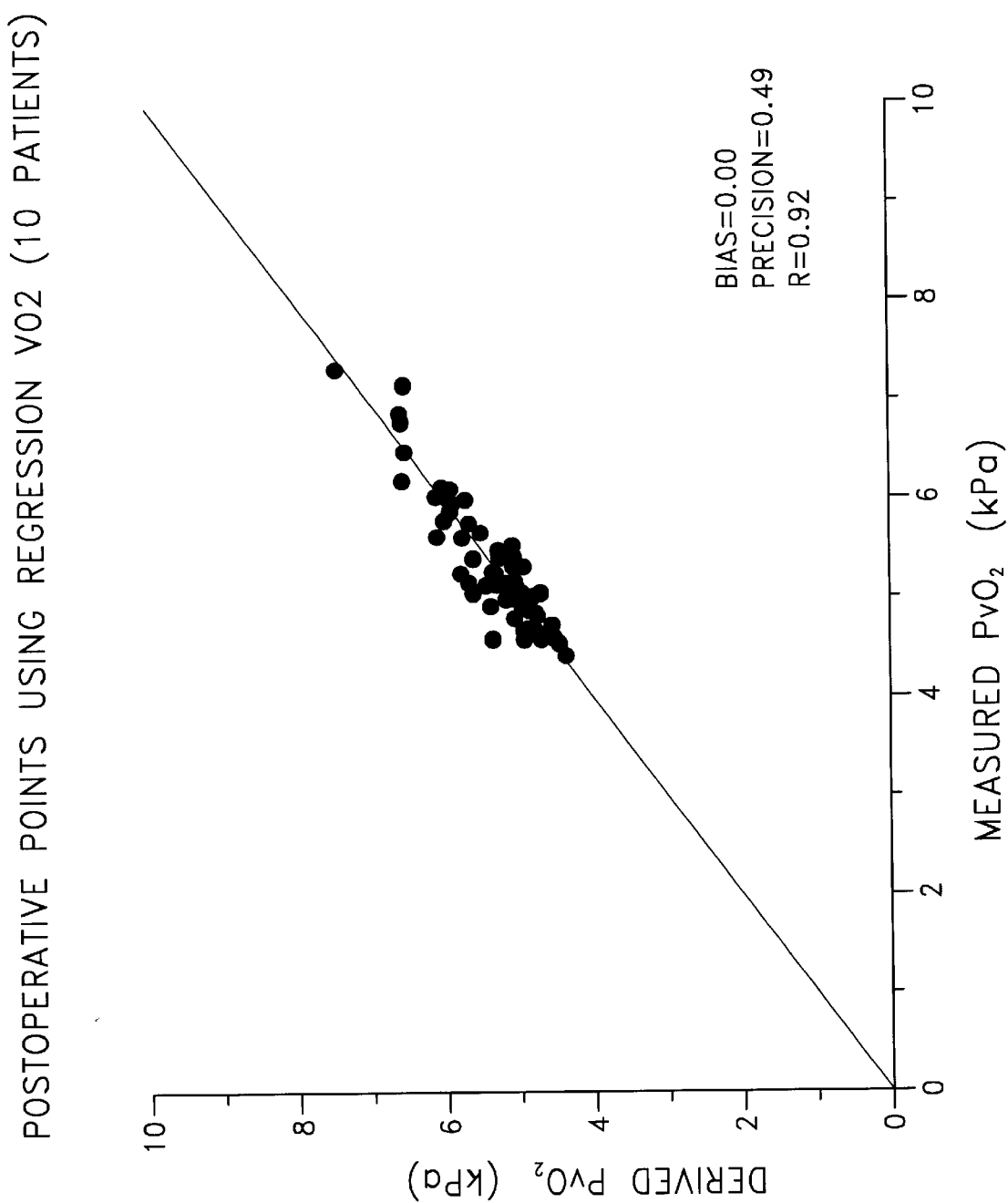
FIG. 6 is a graphical representation of postoperative $PvO_2$ values derived from a PA catheter vs. postoperative $PvO_2$ values derived using the present invention.
Figure 7:
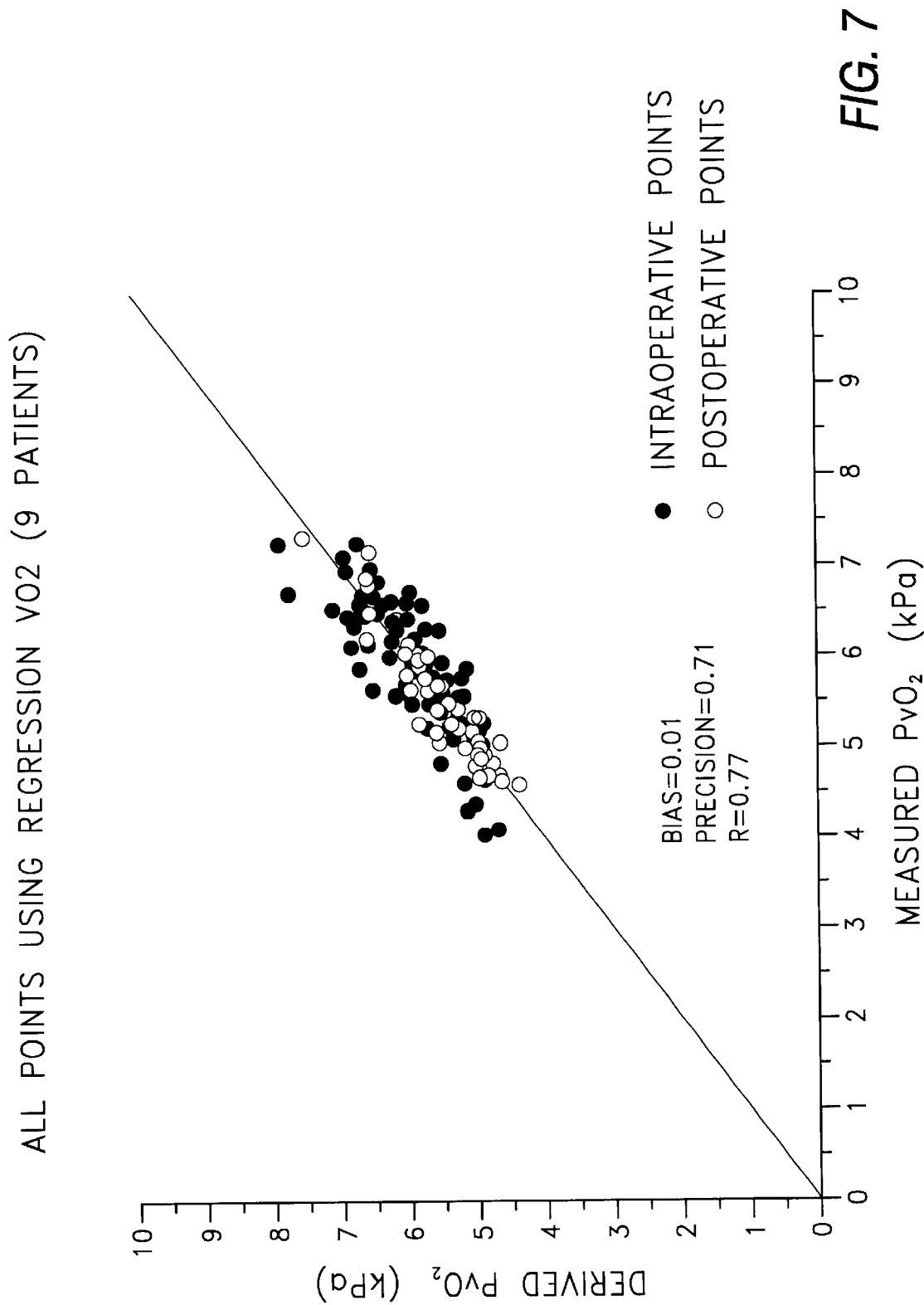
FIG. 7 is a graphical representation combining the $PvO_2$ values from FIGS. 5 & 6.

FIGS. 5, 6 and 7 show the close correlation between measured and derived $PvO_2$ values as reflected by the graphical representation. Derived $PvO_2$ values were generated using regression $VO_2$. FIGS. 5 and 6 represent those values obtained intraoperatively and postoperatively respectively. FIG. 7 illustrates both sets of values.

In particular, the figures illustrate that the derived values closely approximated those measured using conventional, though highly invasive, methods. Accordingly, this example demonstrates that the present invention may be used to provide accurate indications of global tissue oxygenation levels without adversely impacting the patient's condition.

EXAMPLE II

Figure 8:
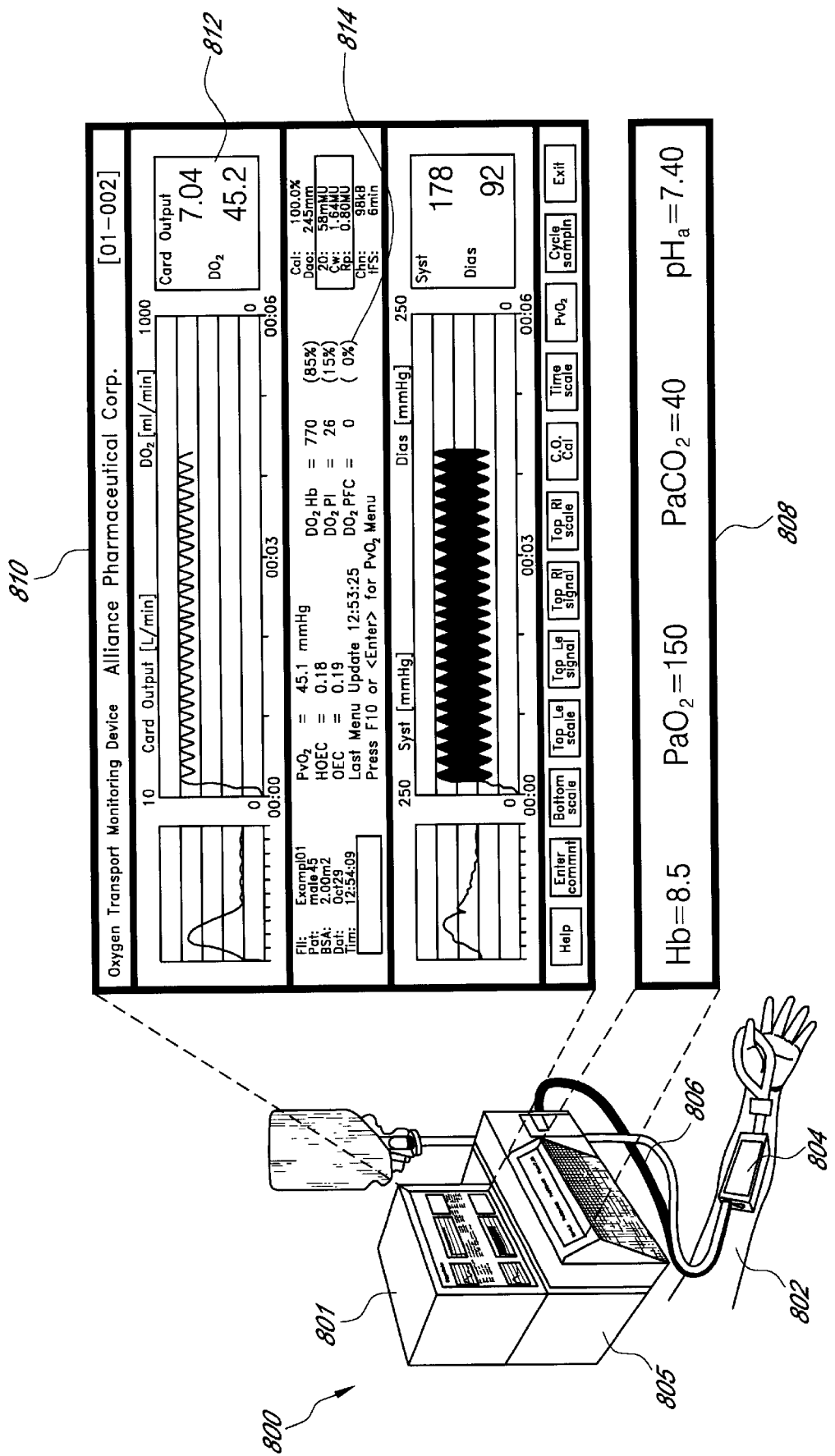
FIG. 8 is an exploded diagram of the present invention showing a representative display screen illustrating the use of the oxygenation parameter $PvO_2$ as an intervention trigger.
Figure 9:
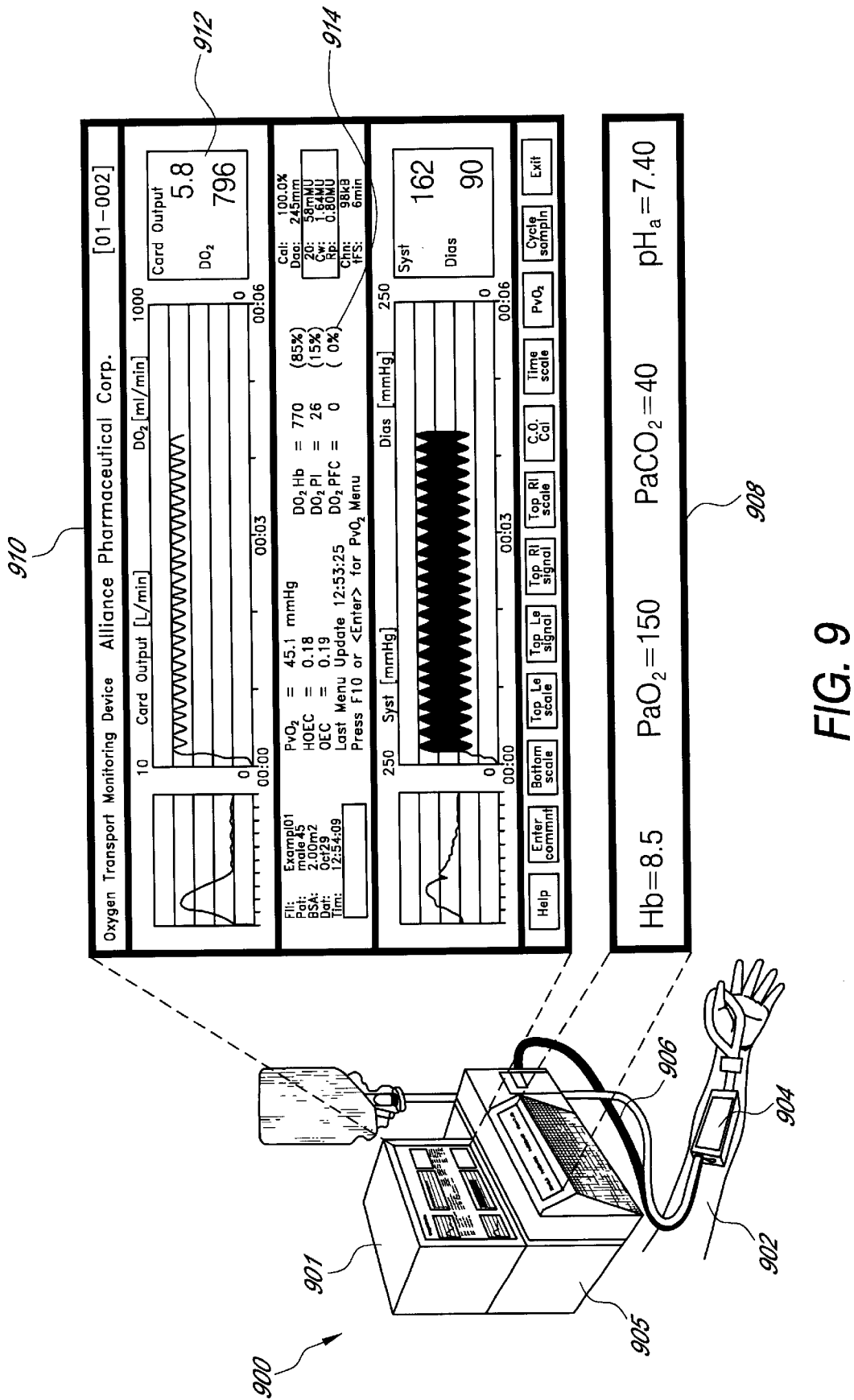
FIG. 9 is an exploded diagram of the present invention showing a representative display screen illustrating the use of the oxygenation parameter $DO_2$ as an intervention trigger.

FIGS. 8 and 9 illustrate exemplary systems, along with video display screens, that are compatible with the teachings herein. In the embodiments shown a blood chemistry monitor and arterial pressure sensor are incorporated within the system. However, it will be appreciated that the integrated systems illustrated are but merely one embodiment and components compatible with the present invention may be assembled in many different configurations.

More particularly, FIG. 8 shows a patient monitoring system 800 comprising, tissue oxygenation monitor 801, blood chemistry monitor 805 and an arterial pressure sensor (not shown) in operable communication. System 800 is operably associated with patient 802 through blood chemistry monitor connector 806. Blood chemistry monitor connector 806 passes information between blood chemistry monitor 805 and blood chemistry sampler 804 which is in fluid conducting communication with the patient's circulatory system. Sampler 804 removes small samples of blood from patient 802, passes it through a row of sensors and returns it relatively quickly to the circulatory system.

As previously described, blood chemistry monitor 805 is obtaining one or more numerical values corresponding to physiological parameters such as hemoglobin concentration, arterial oxygen tension, arterial pH and body temperature. Data obtained from patient 802 is communicated, in real-time, to tissue oxygenation monitor 801 and displayed on blood chemistry monitor display 808. It will be appreciated by those skilled in the art that blood chemistry sampler 804 is relatively non-invasive.

Tissue oxygenation monitor 801 displays data, whether calculated or obtained from blood chemistry monitor 805 or the arterial pressure sensor, through a standard video display terminal to provide data screen 810. While preferred embodiments of the invention will comprise a video display terminal, those skilled in the art will appreciate that the data could be presented in a number of other formats including, for example, strip recordings or print-outs. In this case data screen 810 provides a number of different fields showing, in real-time, graphical representations and numerical values corresponding to the physiological state of the patient.

Several types of standard data are presented such as blood pressure, cardiac output, body temperature, date, etc. It should be emphasized that the illustrated screens are exemplary only and the format or selection of data to be presented is variable and preferably alterable by the clinician.

In any case data screen 810 further provides tissue oxygenation data that was heretofore unavailable using non-invasive procedures. Specifically, data screen 810 provides tissue oxygenation field 812 wherein the patient's mixed venous oxygen tension ($PvO_2$) is displayed. Preferably, this data is updated every second or so and provides the clinician with a continuous, real-time indication of the patient's tissue oxygen status. Of course, it will be appreciated that any (or all) of the disclosed oxygenation parameters, including total oxygen transport ($DO_2$), deliverable oxygen transport ($dDO_2$), mixed venous blood oxyhemoglobin saturation ($SvO_2$), partial venous oxygen pressure ($PvO_2$) and supply/demand ratio ($dDO_2VO_2$) could be displayed if so desired.

Display screen 810 further indicates the oxygenation contributions of the individual oxygen carrying components in circulation. More specifically, component variables 814 are displayed to indicate the relative oxygen transport of hemoglobin, plasma and any blood substitute that has been administered. This data could be particularly useful when performing transfusions or otherwise altering the component concentrations of the circulatory medium.

FIG. 9 is substantially similar to FIG. 8 in that, despite a difference in the displayed data, the embodiment of the apparatus comprises the same components. As such patient monitoring system 900 comprises tissue oxygenation monitor 901, blood chemistry monitor 905 and an arterial pressure sensor (not shown) in operable communication. System 900 is operably associated with patient 902 through blood chemistry monitor connector 906. Blood chemistry monitor connector 906, blood chemistry monitor 905 and blood chemistry sampler 904 work as previously described. As with the previous system data obtained from patient 902 is communicated, in real-time, to tissue oxygenation monitor 901 and displayed on blood chemistry monitor display 908. Similarly tissue oxygenation monitor 901 displays data through a standard video display terminal to provide data screen 910.

While the physical attributes of the systems are identical, the displayed data is somewhat different. Most importantly, the oxygenation parameter selected for monitoring is total oxygen transport $DO_2$ rather than mixed venous oxygen tension $PvO_2$. That is, even though much of the displayed data is the same in FIGS. 8 and 9 (i.e. blood pressure, temperature, etc.), tissue oxygenation field 912 now displays $DO_2$ on a continuous, real-time basis. As discussed, it is preferable that the clinician be able to modify the display and select the data presentation format at will. Accordingly, it is anticipated that the physician will, at any time, be able to "scroll" through or otherwise select any or all of the tissue oxygenation parameters to be displayed.

Similarly, it is anticipated that the physician will be able to select, at will, the display format of the oxygen carrying component variables. In FIG. 9 this feature is illustrated in that component variables 914 now indicate the total oxygen transport of the individual circulatory components rather than the mixed venous oxygen tension as displayed in FIG. 8. Of course it is anticipated that component variables 914 could be displayed using a different oxygenation parameter than the one displayed in tissue oxygenation field 912.

As explained, the present system allows a physician to determine the tissue oxygenation state of a patient, in real time, during surgery or in other clinical settings. The data provided facilitates recognition and diagnosis of potential problems as well as the selection of an effective response. Further, the continuous, real-time monitoring of oxygen status of in tissue allows for the optimization of oxygen transport. In the exemplary embodiments described above, the present invention employs a Microsoft EXCEL® spreadsheet. However, one of ordinary skill in the art could integrate the above-referenced spreadsheet with the Modelflow system or various blood chemistry monitors and still be within the purview of the present invention. For example, software instructions written in other languages such as C++, Cobol, Fortran and basic could also carry out similar functions to the EXCEL® spreadsheet disclosed herein.

Accordingly, those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Thus, the present invention is not limited to the particular embodiments which have been described in detail herein. Rather, reference should be made to the appended claims as indicative of the scope and content of the present invention.

We claim:

1. A relatively non-invasive method for determining, in real-time, one or more physiological parameters indicative of a tissue oxygenation status of a patient, comprising the steps of:

attaching a catheter to an artery of said patient, wherein said catheter is not attached to a pulmonary vein or pulmonary artery;

storing oxygenation constants into a first computer memory;

calculating beat-to-beat cardiac output values (CO) of a patient in real-time, wherein the cardiac output values are saved to a second computer memory;

determining the arterial oxygen content ($CaO_2$) of said patient; and using said cardiac output values and said arterial oxygen content to calculate, in real-time, said one or more parameters indicative of tissue oxygenation status of a patient wherein said parameters are updated often enough to provide a clinically useful indication of the patient's condition.

2. The method of claim 1 wherein said one or more parameters is selected from the group of total oxygen transport ($DO_2$) and deliverable oxygen transport ($dDO_2$).

3. The method of claim 1 farther comprising storing a value corresponding to whole body oxygen consumption ($VO_2$) of said patient into a third computer memory prior to calculating said one or more parameters indicative of tissue oxygenation status of a patient.

4. The method of claim 3 wherein said one or more parameters is selected from the group consisting of total oxygen transport ($DO_2$), deliverable oxygen transport ($dDO_2$), mixed venous blood oxyhemoglobin saturation ($SvO_2$) and mixed venous blood oxygen tension ($PvO_2$).

5. The method of claim 4 wherein said one or more parameters indicative of tissue oxygenation status is calculated by employing an equation having the formula $$(CaO_2 - CvO_2) \times CO = VO_2$$

wherein $CaO_2$ is the arterial oxygen content, $CvO_2$ is the venous oxygen content, CO is the cardiac output and $VO_2$ represents whole body oxygen consumption.

6. The method of claim 3 further comprising calculating a supply/demand ratio ($dDO_2/VO_2$).

7. The method of claim 3 wherein said third computer memory is a random access memory.

8. The method of claim 1 further comprising displaying said one or more parameters on a video display.

9. The method of claim 1 wherein said oxygenation constants comprise one or more numerical values corresponding to at least one of blood volume, oxygen solubility in plasma or oxygen content of a desired unit of saturated oxyhemoglobin.

10. The method of claim 9 wherein said numerical values are determined contemporaneously with said calculating beat-to-beat cardiac output values.

11. The method of claim 1 wherein the arterial oxygen content ($CaO_2$) is determined using one or more numerical values corresponding to hemoglobin concentration, arterial oxygen tension ($PaO_2$), arterial carbon dioxide tension ($PaCO_2$), arterial pH or body temperature of the patient.

12. The method of claim 1 wherein said first computer memory is a random access memory.

13. The method of claim 1 wherein said second computer memory is a random access memory.

14. The method of claim 1 wherein said determining utilizes a blood chemistry monitor.

15. The method of claim 1 wherein said oxygenation constants are obtained from said catheter.

16. A system for non-invasively determining, in real-time, one or more parameters representative of the tissue oxygenation status of a patient, comprising an attachment for measuring oxygen values, adapted to be attached to a patient, wherein said attachment is not to a pulmonary vein or pulmonary artery;

a first computer memory for storing oxygenation constants;

an input derived from said attachment, reflecting beat-to-beat cardiac output (CO) values of a patient in real time, wherein said cardiac output values are saved in a second computer memory;

first instructions for non-invasively obtaining arterial oxygen content ($CaO_2$) of said patient and storing said arterial oxygen content values in a third computer memory; and second instructions for calculating, in real-time, said one or more parameters indicative of tissue oxygenation status of a patient wherein said parameters are derived from said cardiac output values and said arterial oxygen content values and may be updated often enough to provide a clinically useful indication of the patient's condition.

17. The system of claim 16 wherein said one or more parameters representative of the tissue oxygenation status of a patient is selected from the group consisting of total oxygen transport ($DO_2$) and deliverable oxygen transport ($dDO_2$).

18. The system of claim 16 further comprising third instructions for storing a value corresponding to whole body oxygen consumption ($VO_2$) of said patient into a fourth computer memory.

19. The system of claim 18 wherein said one or more parameters representative of the tissue oxygenation status of a patient is selected from the group consisting of total oxygen transport ($DO_2$), deliverable oxygen transport ($dDO_2$), mixed venous blood oxyhemoglobin saturation ($SvO_2$) and mixed venous blood oxygen tension ($PvO_2$).

20. The system of claim 19 wherein said second instructions comprise solving an equation having the formula $$(CaO_2 - CvO_2) \times CO = VO_2$$

wherein $CaO_2$ is the arterial oxygen content, $CvO_2$ is the venous oxygen content, CO is the cardiac output and $VO_2$ represents whole body oxygen consumption.

21. The system of claim 18 wherein said second instructions comprise instructions for calculating a supply/demand ratio ($dDO_2/VO_2$).

22. The system of claim 18 wherein said fourth computer memory is a random access memory.

23. The system of claim 16 wherein said oxygenation constants comprise one or more numerical values corresponding to blood volume, oxygen solubility in plasma or oxygen content of a desired unit of saturated oxyhemoglobin.

24. The system of claim 16 wherein said first instructions comprise obtaining the arterial oxygen content ($CaO_2$) values using one or more numerical values corresponding to hemoglobin concentration, arterial oxygen tension ($PaO_2$), arterial carbon dioxide tension ($PaCO_2$), arterial pH or body temperature of the patient.

25. The system of claim 16 wherein said first computer memory is a random access memory.

26. The system of claim 16 wherein said second computer memory is a random access memory.

27. The system of claim 16 wherein said third computer memory is a random access memory.

28. The system of claim 16 wherein the first, second or third computer memory is a hard disk.

29. The system of claim 16 wherein said attachment comprises an arterial pressure line.

30. The system of claim 16 wherein said first instructions are stored in a blood chemistry monitor.

31. The system of claim 16 wherein said first instructions comprise an application of the Kelman equation.

32. The system of claim 16 wherein said first instructions comprise instructions for obtaining numerical values corresponding to one or more of said patient's hemoglobin concentration, arterial oxygen tension ($PaO_2$), arterial carbon dioxide tension ($CO_2$), arterial pH or body temperature from a keyboard input.

33. The system of claim 16 wherein said first instructions comprise instructions for obtaining numerical values corresponding to one or more of said patient's hemoglobin concentration, arterial oxygen tension ($Pa_2$), arterial carbon dioxide tension ($CO_2$), arterial pH or body temperature from a blood chemistry monitor.

34. A relatively non-invasive method for monitoring, in real-time, tissue oxygenation status of a patient comprising determining a supply/demand ratio ($dDO_2/VO_2$) wherein said supply/demand ratio ($dDO_2/VO_2$) is derived from direct cardiac output values (CO) and arterial oxygen content values ($CaO_2$) obtained in a relatively non-invasive manner wherein said relatively non-invasive manner comprises attaching a catheter to said patient and a monitor for measuring oxygen values, wherein said catheter is not attached to a pulmonary vein or pulmonary artery and wherein said values are updated often enough to provide a clinically useful indication of the patient's condition.

35. A relatively non-invasive apparatus for determining, in real-time, tissue oxygenation status of a patient, said apparatus comprising: a computer memory with instructions for determining the supply/demand ratio ($dDO_2/VO_2$) wherein said supply/demand ratio ($dDO_2/VO_2$) is derived from direct cardiac output values (CO) and arterial oxygen content values ($CaO_2$) obtained in a relatively non-invasive manner, wherein said relatively non-invasive manner comprises attaching a catheter adapted to be attached to a patient, but not attached to a pulmonary vein or pulmonary artery of said patient, and wherein said values may be updated often enough to provide a clinically useful indication of the patient's condition.

\* \* \* \* \*